(12) United States Patent
Hu

(10) Patent No.: US 11,877,881 B2
(45) Date of Patent: *Jan. 23, 2024

(54) SYSTEM AND METHOD FOR NOISE REDUCTION

(71) Applicant: SHANGHAI UNITED IMAGING HEALTHCARE CO., LTD., Shanghai (CN)

(72) Inventor: Lingzhi Hu, Houston, TX (US)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/049,284

(22) Filed: Oct. 24, 2022

(65) Prior Publication Data

US 2023/0074019 A1 Mar. 9, 2023

Related U.S. Application Data

(63) Continuation of application No. 16/870,908, filed on May 9, 2020, now Pat. No. 11,478,211.

(60) Provisional application No. 62/943,198, filed on Dec. 3, 2019.

(51) Int. Cl.
*A61B 6/00* (2006.01)
*G01R 33/385* (2006.01)

(52) U.S. Cl.
CPC ........ *A61B 6/5258* (2013.01); *G01R 33/3854* (2013.01); *A61B 2560/0462* (2013.01)

(58) Field of Classification Search
CPC .......... A61B 6/5258; A61B 2560/0462; G01R 33/3854; G01R 33/288; G10K 11/1787; G10K 11/17879
See application file for complete search history.

(56) References Cited

U.S. PATENT DOCUMENTS

| 5,427,102 A | 6/1995 | Shimode et al. |
| 6,463,316 B1 | 10/2002 | Brungart |
| 6,954,666 B2 | 10/2005 | Bechtold et al. |
| 2005/0246346 A1 | 11/2005 | Sellers |

(Continued)

FOREIGN PATENT DOCUMENTS

| CN | 101261829 A | 9/2008 |
| CN | 104622470 A | 5/2015 |

(Continued)

OTHER PUBLICATIONS

First Office Action in Chinese Application No. 202010528912.1 dated Jun. 28, 2022, 31 pages.

*Primary Examiner* — Peter Luong
(74) *Attorney, Agent, or Firm* — METIS IP LLC

(57) ABSTRACT

The present disclosure provides a system for active noise cancellation for a subject placed in a scanning bore of a medical imaging apparatus. The system may be directed to perform operations including obtaining a real-time position of each of at least one target portion of a subject; obtaining signals from one or more arrays of noise detection units surrounding the subject; and directing, based on the signals obtained from the one or more arrays of noise detection units, one or more arrays of denoising units to produce a sound to counteract noise at the real-time position of each of the at least one target portion of the subject.

20 Claims, 13 Drawing Sheets

(56) References Cited

U.S. PATENT DOCUMENTS

| | | | |
|---|---|---|---|
| 2013/0154647 A1* | 6/2013 | Yang | G01R 33/283 |
| | | | 324/318 |
| 2015/0100310 A1 | 4/2015 | Cha et al. | |
| 2016/0314778 A1 | 10/2016 | Christoph et al. | |
| 2018/0113181 A1 | 4/2018 | Popescu | |

FOREIGN PATENT DOCUMENTS

| | | |
|---|---|---|
| CN | 107564509 A | 1/2018 |
| CN | 110222843 A | 9/2019 |

* cited by examiner

SYSTEM AND METHOD FOR NOISE REDUCTION

CROSS-REFERENCE OF RELATED APPLICATION

This application is a Continuation of U.S. patent application Ser. No. 16/870,908, filed May 9, 2020, which claims the benefit of U.S. Provisional Patent Application No. 62/943,198, filed Dec. 3, 2019, the contents of which are hereby incorporated by reference.

TECHNICAL FIELD

This disclosure generally relates to a noise reduction technique applied to a medical apparatus, and more particularly, to systems and methods for cancelling noises at a target position in the medical device (e.g., an MRI apparatus) based on an active noise cancellation (ANC) technique.

BACKGROUND

Magnetic resonance imaging (MRI) is a widely used medical technique which produces images of a region of interest (ROI) by exploiting a powerful magnetic field and radio frequency (RF) techniques. A subject (e.g., a patient or a body part thereof) can be placed in a scanning region of an MRI scanner so that the MRI scanner can scan the subject in an imaging session or deliver a radiation dose to the subject in a radiotherapy treatment. During the imaging session or the radiotherapy treatment, one or more components of the MRI scanner usually produce noises, which may cause discomfort to the subject. In addition, a slight motion of the subject due to the noises may have a negative impact on the imaging quality or the effect of the radiotherapy treatment. Therefore, it is desirable to develop systems and methods for reducing the noises within the scanning region.

SUMMARY

According to an aspect of the present disclosure, a system for active noise cancellation for a subject placed in a scanning bore of a medical imaging apparatus may be provided. The system may comprise at least one storage device including a set of instructions, and at least one processor configured to communicate with the at least one storage device. When executing the set of instructions, the at least one processor is configured to direct the system to perform operations including detecting first noise signals by a first array of noise detection units disposed in the scanning bore, at least part of the first noise signals resulting from an operation of gradient coils of the medical imaging apparatus; detecting, by a second array of noise detection units, second noise signals near a target position associated with the subject; and determining anti-noise signals based on the first noise signals, the second noise signals and excitation signals used for the operation of the medical imaging apparatus.

In some embodiments, the at least one processor is further configured to direct the system to perform the operations including generating, via one or more denoising units, sounds in accordance with the anti-noise signals.

In some embodiments, the generating, via one or more denoising units, sounds in accordance with the anti-noise signals includes selecting all or a portion of the one or more denoising units based on properties of the anti-noise signals; and directing the selected denoising units to generate the sounds in accordance with the anti-noise signals.

In some embodiments, at least one of the one or more denoising units are fitted to a support platform for supporting the subject and near the target position.

In some embodiments, at least one of the one or more denoising units are fitted on a local coil associated with the target position.

In some embodiments, the one or more denoising units include one or more vibration components for generating the sounds in accordance with the anti-noise signals.

In some embodiments, the one or more denoising units include one or more directional speakers configured to transmit the sounds along a certain direction towards the target position in accordance with the anti-noise signals.

In some embodiments, the determining the anti-noise signals based on the first noise signals, the second noise signals and the excitation signals includes determining predicted noise signals near the target position by feeding the first noise signals, the second noise signals and the excitation signals to a target noise prediction model; and determining the anti-noise signals based on the predicted noise signals, wherein the anti-noise signals have an opposite phase to the predicted noise signals.

In some embodiments, the determining the anti-noise signals based on the first noise signals, the second noise signals and the excitation signals includes designating the first noise signals and the excitation signals as feedforward input signals of an FXLMS algorithm based noise cancellation model; designating the second noise signals as feedback input signals of the FXLMS algorithm based noise cancellation model; and determining, based on the FXLMS algorithm based noise cancellation model, the anti-noise signals by minimizing the second noise signals.

In some embodiments, the at least one processor is configured to direct the system to perform the operations including determining the target position associated with the subject based on information obtained by a locating unit operably coupled with the medical imaging apparatus; determining, based on the first noise signals and the second noise signals, a noise level at the target position with a sound field simulation model; and determining the anti-noise signals based on the noise level.

In some embodiments, the medical imaging apparatus includes a magnetic resonance imaging (MRI) apparatus, and the noise detection device includes a non-magnetic microphone.

According to another aspect of the present disclosure, a medical imaging apparatus may be provided. The medical imaging apparatus may include a scanning bore configured to accommodate a subject to be imaged and a support platform for supporting the subject; gradient coils configured to generate gradient magnetic fields; a first array of noise detection units disposed in the scanning bore and configured to detect first noise signals, at least part of the first noise signals resulting from an operation of the gradient coils; a second array of noise detection units disposed near a target position associated with the subject and detect second noise signals; a processing circuit configured to determine anti-noise signals based on the first noise signals, the second signals and excitation signals used for the operation of the gradient coils; and one or more denoising units configured to generate sounds in accordance with the anti-noise signals.

In some embodiments, all or a portion of the one or more denoising units are selected based on properties of the anti-noise signals, and the selected denoising units are directed to generate the sounds in accordance with the anti-noise signals.

In some embodiments, at least one of the one or more denoising units are fitted to the support platform for supporting the subject and near the target position.

In some embodiments, at least one of the one or more denoising units are fitted on a radio frequency (RF) coil associated with the target position.

In some embodiments, the one or more denoising units include one or more vibration components for generating the sounds in accordance with the anti-noise signals.

In some embodiments, the one or more denoising units include one or more directional speakers configured to transmit the sounds along a certain direction towards the target position in accordance with the anti-noise signals.

In some embodiments, to determine anti-noise signals based on the first noise signals, the second signals and the excitation signals used for the operation of the gradient coils, the processing circuit is further configured to determine predicted noise signals near the target position by feeding the first noise signals, the second noise signals and the excitation signals to a target noise prediction model; and determine the anti-noise signals based on the predicted noise signals, wherein the anti-noise signals have an opposite phase to the predicted noise signals.

In some embodiments, to determine anti-noise signals based on the first noise signals, the second signals and the excitation signals used for the operation of the gradient coils, the processing circuit is further configured to designate the first noise signals and the excitation signals as feedforward input signals of an FXLMS algorithm based noise cancellation model; designate the second noise signals as feedback input signals of the FXLMS algorithm based noise cancellation model; and determine, based on the FXLMS algorithm based noise cancellation model, the anti-noise signals by minimizing the second noise signals.

In some embodiments, the processing circuit is further configured to determine the target position associated with the subject based on information obtained by a locating unit operably coupled with the medical imaging apparatus; determine, based on the first noise signals and the second noise signals, a noise level at the target position with a sound field simulation model; and determine the anti-noise signals based on the noise level.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," "module," and/or "block" used herein are one method to distinguish different components, elements, parts, section or assembly of different level in ascending order. However, the terms may be displaced by another expression if they may achieve the same purpose.

Figure 3:
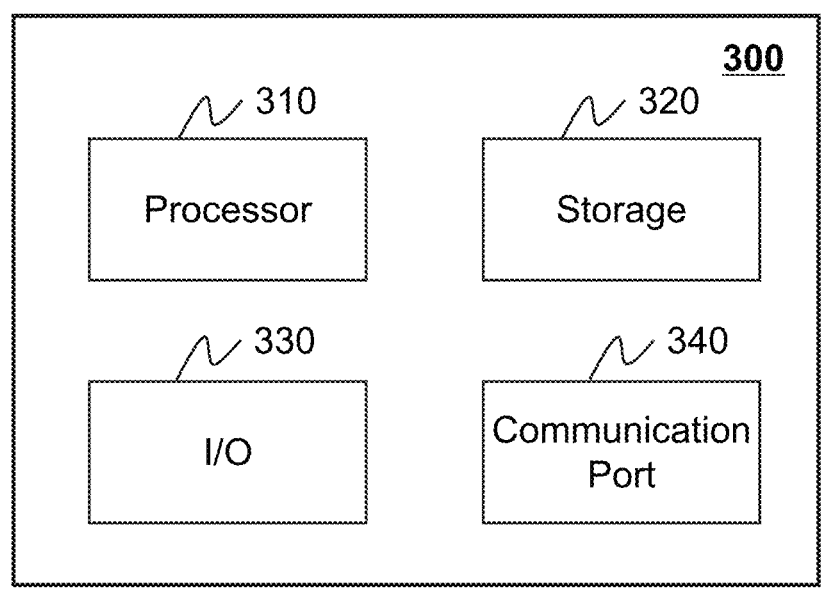
FIG. 3 is a schematic diagram illustrating exemplary hardware and/or software components of a computing device on which the processing device may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or another storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 310 as illustrated in FIG. 3) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an Erasable Programmable Read Only Memory (EPROM). It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary MRI systems may include a superconducting magnetic resonance imaging system, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction magnetic resonance imaging (DSA-MRI) system, etc.

Various embodiments of the present disclosure can be provided for noise cancellation or noise reduction. In some embodiments, when a subject (e.g., a patient) is placed in the scanning region of a scanning device (e.g., an MRI scanner) for an imaging scan or radiotherapy treatment, a noise cancellation system provided herein may be implemented in order to reduce or eliminate the acoustic noises occurred in the scanning region or one or more sub-regions therein. In some embodiments, the noise cancellation system may include a locating unit for identifying and determining a target position associated with the subject, such as a position of ears of a patient. The noise cancellation system may include a first array of noise detection units and a second array of noise detection units. The first array of noise detection units may be configured to detect first noise signals inside the scanning region, which are acoustic noises resulting from an operation of gradient coils of the scanning device, such as the vibration caused during the MRI scan. The second array of noise detection units may be configured to detect second noise signals may be configured to detect second noise signals near (or around) the target position. In some embodiments, the second array of noise detection units may be disposed close to at least one target position (e.g., ears of the subject) relative to other positions of the subject. In some embodiments, the second noise signals may be a portion of noise signals being close to the at least one target position. The second noise signals may include error noise signals, which is the net response of the original acoustic noises (e.g., the first noise signals) and sounds produced by one or more denoising units. In some embodiments, the noise cancellation system may include or be in association with a computing device (e.g., a processing device or a processing circuit). The computing device may obtain excitation signals (e.g., gradient pulse sequences) used for the operation of the gradient coils. The computing device may determine anti-noise signals by processing the first noise signals, the second noise signals and the excitation signals. In some embodiments, the noise cancellation system may include one or more denoising units. The one or more denoising units may be directed to generate sounds for cancelling the noises arriving at the target position in accordance with the anti-noise signals, for example, one or more denoising parameters indicative of the anti-noise signals. The generated sounds may have an opposite phase to the phase of the noises arriving at the target position in order to counteract the noises. It should be noted that the noise cancellation system may be integrated to the scanning device and as part of the scanning device.

Figure 1:
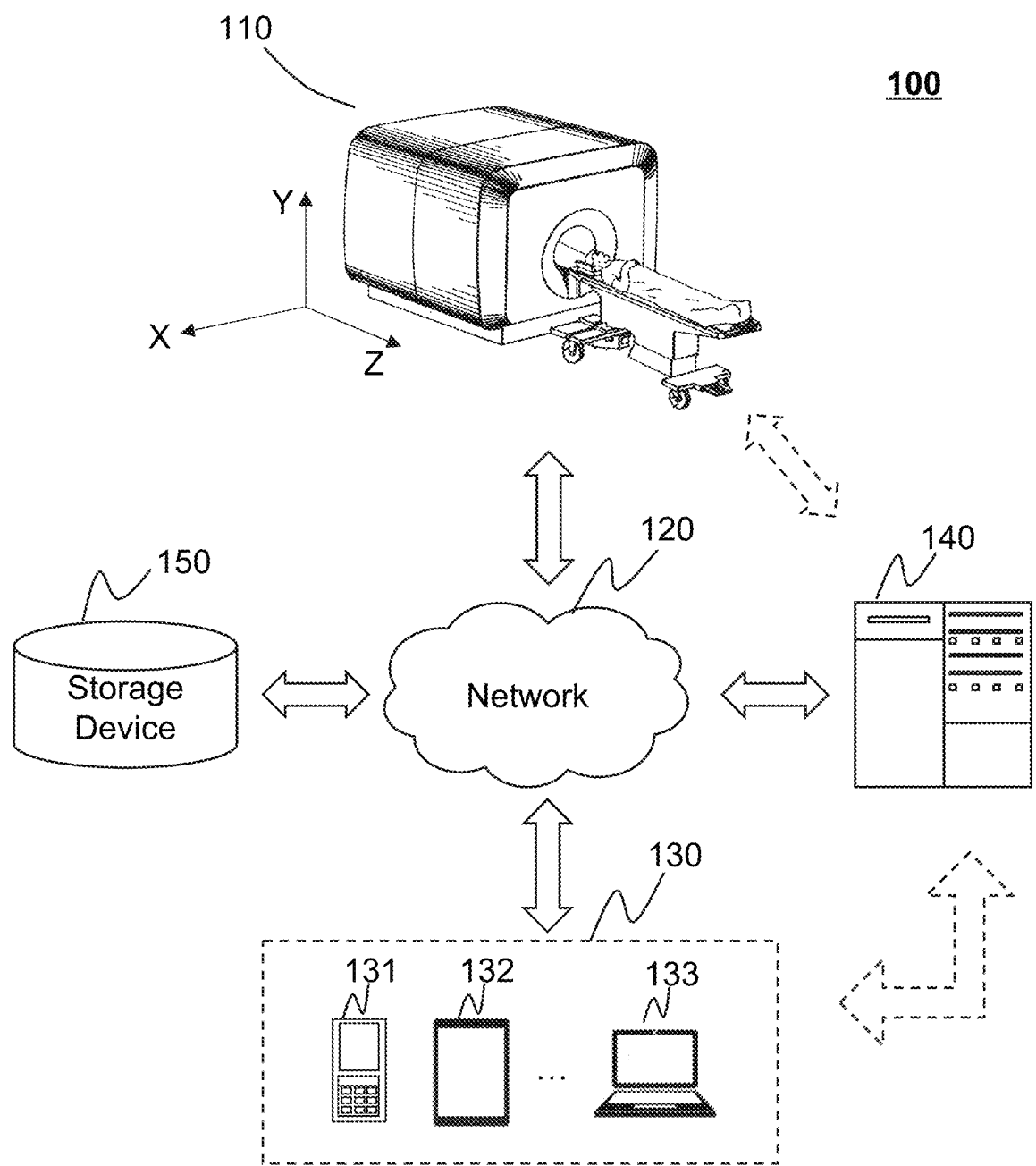
FIG. 1 is a schematic diagram illustrating an exemplary imaging system according to some embodiments of the present disclosure.

FIG. 1 is a schematic diagram illustrating an exemplary imaging system according to some embodiments of the present disclosure. As used herein, the imaging system may be an MRI system. As illustrated, the imaging system 100 may include an MRI apparatus 110, a network 120, a terminal 130, a processing device 140, and a storage device 150. The components of the imaging system 100 may be connected in one or more of various ways. Mere by way of example, as illustrated in FIG. 1, the MRI apparatus 110 may be connected to the processing device 140 through the network 120. As another example, the MRI apparatus 110 may be connected to the processing device 140 directly (as indicated by the bi-directional arrow in dotted lines linking the MRI apparatus 110 and the processing device 140). As a further example, the storage device 150 may be connected to the processing device 140 directly or through the network 120. As still a further example, a terminal device (e.g., 131, 132, 133, etc.) may be connected to the processing device 140 directly (as indicated by the bi-directional arrow in dotted lines linking the terminal 130 and the processing device 140) or through the network 120.

The MRI apparatus 110 may scan an object located within its detection region and generate a plurality of data relating to the object. In the present disclosure, "subject" and "object" are used interchangeably. Mere by way of example, the object may include a patient, a man-made object, etc. As another example, the object may include a specific portion, organ, and/or tissue of a patient. For example, the object may include head, brain, neck, body, shoulder, arm, thorax, heart, stomach, blood vessel, soft tissue, knee, feet, or the like, or any combination thereof. In some embodiments, the MRI apparatus 110 may be a close-bore scanner or an open-bore scanner. In the present disclosure, the X axis, the Y axis, and the Z axis shown in FIG. 1 may form an orthogonal coordinate system. The X axis and the Z axis shown in FIG. 1 may be horizontal, and the Y axis may be vertical. As illustrated, the positive X direction along the X axis may be from the right side to the left side of the MRI apparatus 110 seen from the direction facing the front of the MRI apparatus 110; the positive Y direction along the Y axis shown in FIG. 1 may be from the lower part to the upper part of the MRI apparatus 110; the positive Z direction along the Z axis shown in FIG. 1 may refer to a direction in which the object is moved out of the scanning channel (or referred to as the bore) of the MRI apparatus 110. More description of the MRI apparatus 110 may be found elsewhere in the present disclosure. See, e.g., FIG. 2 and the description thereof.

The network 120 may include any suitable network that can facilitate the exchange of information and/or data for the imaging system 100. In some embodiments, one or more components of the imaging system 100 (e.g., the MRI apparatus 110, the terminal 130, the processing device 140, or the storage device 150) may communicate information and/or data with one or more other components of the imaging system100 via the network 120. For example, during operation of imaging system 100 (e.g., during an imaging scan of the MRI apparatus 110), the processing device 140 may obtain excitation signals (e.g., pulse sequences) used for the operation of gradient coils in the MRI apparatus 110 via the network 120. In some embodiments, the network 120 may be any type of wired or wireless network, or a combination thereof. The network 120 may be and/or include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN),a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal 130 may include a mobile device 131, a tablet computer 132, a laptop computer 133, or the like, or any combination thereof. In some embodiments, the mobile device 131 may include a smart home device, a wearable device, a smart mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a smart bracelet, smart footgear, a pair of smart glasses, a smart helmet, a smart watch, smart clothing, a smart backpack, a smart accessory, or the like, or any combination thereof. In some embodiments, the smart mobile device may include a smartphone, a personal digital assistant (PDA), a gaming device, a navigation device, a point of sale (POS) device, or the like, or any combination thereof. In some embodiments, the virtual reality device and/or the augmented reality device may include a virtual reality helmet, a virtual reality glass, a virtual reality patch, an augmented reality helmet, an augmented reality glass, an augmented reality patch, or the like, or any combination thereof. For example, the virtual reality device and/or the augmented reality device may include a Google™ Glass, an Oculus Rift, a Hololens, a Gear VR, etc. In some embodiments, the terminal 130 may remotely operate the MRI apparatus 110 and/or the processing device 140. In some embodiments, the terminal 130 may operate the MRI apparatus 110 and/or the processing device 140 via a wireless connection. In some embodiments, the terminal 130 may receive information and/or instructions inputted by a user, and send the received information and/or instructions to the MRI apparatus 110 or to the processing device 140 via the network 120. In some embodiments, the terminal 130 may receive data and/or information from the processing device 140. In some embodiments, the terminal 130 may be part of the processing device 140. In some embodiments, the terminal 130 may be omitted.

The processing device 140 may process data and/or information obtained from the MRI apparatus 110, the terminal 130, and/or the storage device 150. In some embodiments, a noise cancellation system may be integrated to the MRI apparatus 100. The MRI apparatus 110 may include a first array of noise detection units (e.g., a first microphone array) configured to detect first noise signals within the scanning bore of the MRI apparatus 110. At least part of the first noise signals results from the operation of the gradient coils of the MRI apparatus 110. In some embodiments, the MRI apparatus 100 may include a second array of noise detection units (e.g., a second microphone array)

configured to detect second noise signals near (or around) a target position associated with a subject (e.g., a position of the ears of a patient). The processing device 140 may determine anti-noise signals based on the first noise signals, the second noise signals and the excitation signals used for the operation of gradient coils. In response to the anti-noise signals, one or more denoising units may be directed to produce sounds to cancel the noises arriving at the target position, thereby a regional quite zone covering the target position can be formed.

In some embodiments, the processing device 140 may be a single server, or a server group. The server group may be centralized or distributed. In some embodiments, the processing device 140 may be local or remote. For example, the processing device 140 may access information and/or data stored in or acquired by the MRI apparatus 110, the terminal 130, and/or the storage device 150 via the network 120. As another example, the processing device 140 may be directly connected to the MRI apparatus 110 (as illustrated by the bidirectional arrow in dashed lines connecting the processing device 140 and the MRI apparatus 110 in FIG. 1), the terminal 130 (as illustrated by the bidirectional arrow in dashed lines connecting the processing device 140 and the terminal 130 in FIG. 1), and/or the storage device 150 to access stored or acquired information and/or data. In some embodiments, the processing device 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing device 140 may be implemented on a computing device 300 having one or more components illustrated in FIG. 3 in the present disclosure.

The storage device 150 may store data and/or instructions. In some embodiments, the storage device 150 may store data obtained from the MRI apparatus 110, the terminal 130 and/or the processing device 140. For example, the storage device 150 may store noise signals (e.g., the first noise signals and the second noise signals) detected in the MRI apparatus 110. In some embodiments, the storage device 150 may store data and/or instructions that the processing device 140 may execute or use to perform exemplary methods described in the present disclosure. For example, the storage device 150 may store instructions that the processing device 140 may execute to perform one or more operations for generating anti-noise signals for actively cancelling the noises around the target position. In some embodiments, the storage device 150 may include a mass storage device, a removable storage device, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random-access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage device 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage device 150 may be connected to the network 120 to communicate with one or more components of the imaging system 100 (e.g., the MRI apparatus 110, the processing device 140, the terminal 130, etc.). One or more components of the imaging system 100 may access the data or instructions stored in the storage device 150 via the network 120. In some embodiments, the storage device 150 may be directly connected to or communicate with one or more components of the imaging system 100 (e.g., the MRI apparatus 110, the processing device 140, the terminal 130, etc.). In some embodiments, the storage device 150 may be part of the processing device 140.

In some embodiments, the imaging system 100 may further include one or more power supplies (not shown in FIG. 1) connected to one or more components of the imaging system 100 (e.g., the MRI apparatus 110, the processing device 140, the terminal 130, the storage device 150, etc.).

Figure 2:
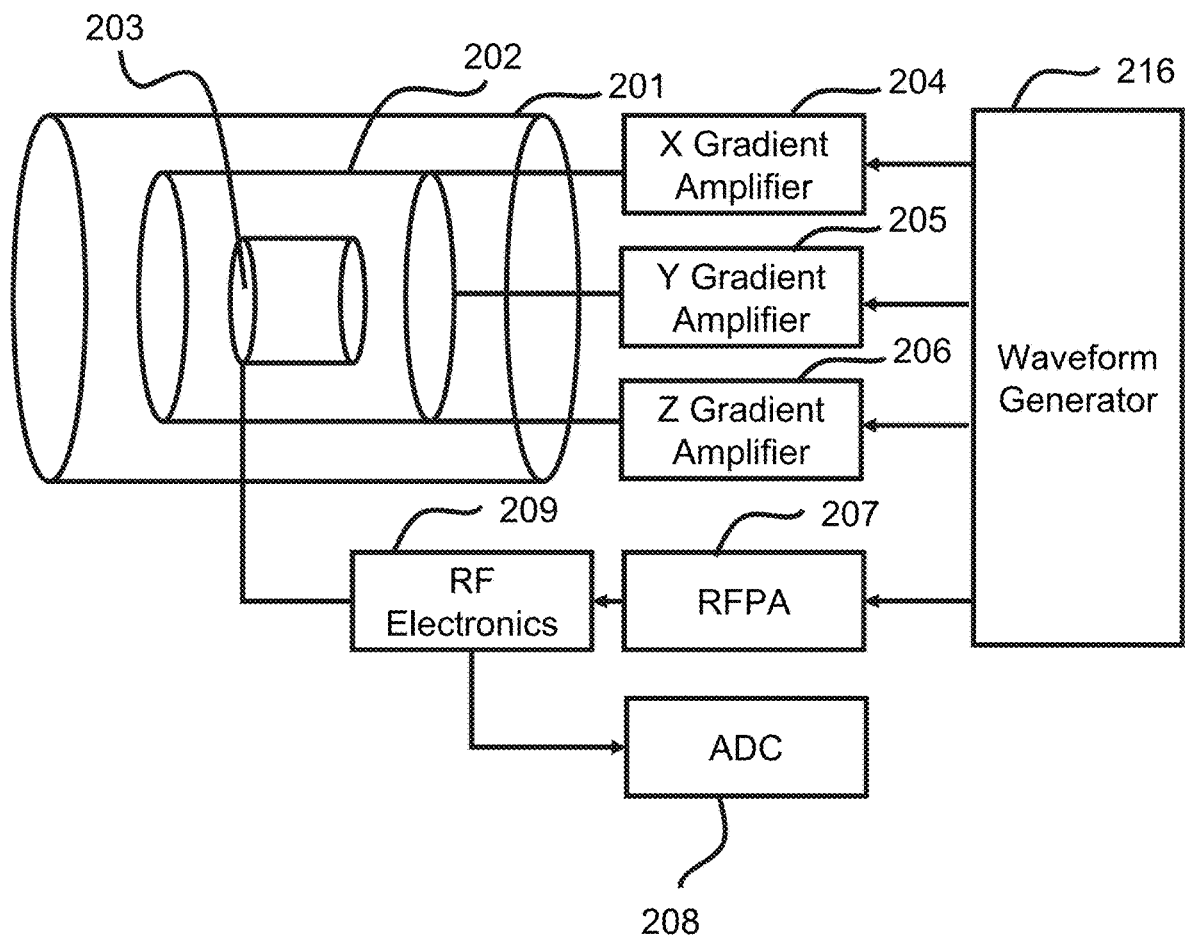
FIG. 2 is a schematic diagram illustrating an exemplary MRI apparatus according to some embodiments of the present disclosure.

FIG. 2 is a schematic diagram illustrating an exemplary MRI apparatus (or an MRI scanner) according to some embodiments of the present disclosure. One or more components of the MRI apparatus 110 are illustrated in FIG. 2. As illustrated, main magnet 201 may generate a first magnetic field (also referred to as a main magnetic field) that may be applied to an object (also referred to as a subject) exposed inside the field. The main magnet 201 may include a resistive magnet or a superconductive magnet that both need a power supply (not shown) for operation. Alternatively, the main magnet 201 may include a permanent magnet. The main magnet 201 may include a bore (or referred to as a scanning bore) that the object is placed within. The scanning bore may be configured to accommodate the subject to be imaged and a support platform (not shown in FIG. 2) for supporting the subject. The support platform may be driven to move inside or outside of the scanning bore. The main magnet 201 may also control the homogeneity of the generated main magnetic field. Some shim coils may be in the main magnet 201. The shim coils placed in the gap of the main magnet 201 may compensate for the inhomogeneity of the magnetic field of the main magnet 201. The shim coils may be energized by a shim power supply.

Gradient coils 202 may be located inside the main magnet 201. The gradient coils 202 may generate a second magnetic field (or referred to as a gradient field, including gradient fields Gx, Gy, and Gz). The second magnetic field may be superimposed on the main field generated by the main magnet 201 and distort the main field so that the magnetic orientations of the protons of an object may vary as a function of their positions inside the gradient field, thereby encoding spatial information into MR signals generated by the region of the object being imaged. The gradient coils 202 may include X coils (e.g., configured to generate the gradient field Gx corresponding to the X direction), Y coils (e.g., configured to generate the gradient field Gy corresponding to the Y direction), and/or Z coils (e.g., configured to generate the gradient field Gz corresponding to the Z direction) (not shown in FIG. 2). In some embodiments, the Z coils may be designed based on circular (Maxwell) coils, while the X coils and the Y coils may be designed on the basis of the saddle (Golay) coil configuration. The three sets of coils may generate three different magnetic fields that are used for position encoding. The gradient coils 202 may allow spatial encoding of MR signals for image construction. The gradient coils 202 may be connected with one or more of an X gradient amplifier 204, a Y gradient amplifier 205, or a Z gradient amplifier 206. One or more of the three amplifiers may be connected to a waveform generator 216. The waveform generator 216 may generate gradient waveforms (or gradient pulse sequences) that are applied to the X gradient amplifier 204, the Y gradient amplifier 205, and/or the Z gradient amplifier 206. An amplifier may amplify a waveform. An amplified waveform may be applied to one of the coils in the gradient coils 202 to generate a magnetic field in the X-axis, the Y-axis, or the Z-axis, respectively. The gradient coils 202 may be designed for either a close-bore MRI scanner or an open-bore MRI scanner. In some instances, all three sets of coils of the gradient coils 202 may be energized and three gradient fields may be generated thereby. In some embodiments of the present disclosure, the X coils and Y coils may be energized to generate the gradient fields in the X direction and the Y direction. As used herein, the X-axis, the Y-axis, the Z-axis, the X direction, the Y direction, and the Z direction in the description of FIG. 2 are the same as or similar to those described in FIG. 1.

During the scan of the MRI apparatus 110, a sudden change in current within a gradient coil of the gradient coils in the presence of a static magnetic field may produce a strong Lorentz force on the gradient coil. Noises may be generated in the MRI apparatus 110 when the force causes motion and vibrations in the gradient coil. MRI noises may arise from various sources. For example, pulse sequences, such as fast gradient echo (FGE), echo planar imaging (EPI), and fast spin echo (FSE) sequences requiring extremely fast switching of gradient magnetic fields and high gradient fields, may generate high levels of noise. A level of noise generated during the MRI scan may rely on the type of a pulse sequence used for the operation of the gradient coils 202. In some embodiments, excitation signals used for the operation of the gradient coils 202 should be taken into consideration to suppress the noises.

In some embodiments, radio frequency (RF) coils 203 may be located inside the main magnet 201 and serve as transmitters, receivers, or both. The RF coils 203 may be in connection with RF electronics 209 that may be configured or used as one or more integrated circuits (ICs) functioning as a waveform transmitter and/or a waveform receiver. The RF electronics 209 may be connected to a radiofrequency power amplifier (RFPA) 207 and an analog-to-digital converter (ADC) 208.

When used as transmitters, the RF coils 203 may generate RF signals that provide a third magnetic field that is utilized to generate MR signals related to the region of the object being imaged. The third magnetic field may be perpendicular to the main magnetic field. The waveform generator 216 may generate an RF pulse. The RF pulse may be amplified by the RFPA 207, processed by the RF electronics 209, and applied to the RF coils 203 to generate the RF signals in response to a powerful current generated by the RF electronics 209 based on the amplified RF pulse.

When used as receivers, the RF coils may be responsible for detecting MR signals (e.g., echoes). After excitation, the MR signals generated by the object may be sensed by the RF coils 203. The receive amplifier then may receive the sensed MR signals from the RF coils 203, amplify the sensed MR signals, and provide the amplified MR signals to the ADC 208. The ADC 208 may transform the MR signals from analog signals to digital signals. The digital MR signals may be filled to a k-space based on a predetermined k-space sampling scheme. In some embodiments, the k-space data may be sent to the processing device 140 for further reconstructing.

In some embodiments, the gradient coils 202 and the RF coils 203 may be circumferentially positioned with respect to the object. It is understood by those skilled in the art that the main magnet 201, the gradient coils 202, and the RF coils 203 may be situated in a variety of configurations around the object.

In some embodiments, the RFPA 207 may amplify an RF pulse (e.g., the power of the RF pulse, the voltage of the RF pulse) such that an amplified RF pulse is generated to drive the RF coils 203. The RFPA 207 may include a transistor-based RFPA, a vacuum tube-based RFPA, or the like, or any combination thereof. The transistor-based RFPA may include one or more transistors. The vacuum tube-based RFPA may include a triode, a tetrode, a klystron, or the like, or any combination thereof. In some embodiments, the RFPA 207 may include a linear RFPA, or a nonlinear RFPA. In some embodiments, the RFPA 207 may include one or more RFPAs.

In some embodiments, the MRI apparatus 110 may further include an object positioning system (not shown). The object positioning system may include a support platform and a transport device. The object may be placed on the support platform and be positioned by the transport device within the bore of the main magnet 201.

FIG. 3 is a schematic diagram illustrating exemplary hardware and/or software components of a computing device on which a processing device may be implemented according to some embodiments of the present disclosure. As illustrated in FIG. 3, computing device 300 may include a processor 310, a storage 320, an input/output (I/O) 330, and a communication port 340.

The processor 310 may execute computer instructions (or program codes) and perform functions of the processing device 140 in accordance with techniques described herein. The computer instructions may include routines, programs, objects, components, signals, data structures, procedures, modules, and functions, which perform particular functions described herein. For example, the processor 310 may generate anti-noise signals by processing first noise signals, second noise signals and excitation signals used for the operation of gradient coils (e.g., the gradient coils 202). In some embodiments, the processor 310 may include a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combinations thereof.

Merely for illustration purposes, only one processor is described in the computing device 300. However, it should be noted that the computing device 300 in the present disclosure may also include multiple processors, and thus operations of a method that are performed by one processor as described in the present disclosure may also be jointly or separately performed by the multiple processors. For example, if in the present disclosure the processor of the computing device 300 executes both operations A and B, it should be understood that operations A and step B may also be performed by two different processors jointly or separately in the computing device 300 (e.g., a first processor executes operation A and a second processor executes operation B, or the first and second processors jointly execute operations A and B).

The storage 320 may store data/information obtained from the MRI apparatus 110, the terminal 130, the storage device 150, or any other component of the MRI system 100. In some embodiments, the storage 320 may include a mass storage device, a removable storage device, a volatile read-and-write memory, a read-only memory (ROM), or the like, or any combination thereof. For example, the mass storage device may include a magnetic disk, an optical disk, a solid-state drive, etc. The removable storage device may include a flash drive, a floppy disk, an optical disk, a memory card, a zip disk, a magnetic tape, etc. The volatile read-and-write memory may include a random-access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (PEROM), an electrically erasable programmable ROM (EEPROM), a compact disk ROM (CD-ROM), and a digital versatile disk ROM, etc. In some embodiments, the storage 320 may store one or more programs and/or instructions to perform exemplary methods described in the present disclosure.

The I/O 330 may input or output signals, data, or information. In some embodiments, the I/O 330 may enable user interaction with the processing device 140. In some embodiments, the I/O 330 may include an input device and an output device. Exemplary input devices may include a keyboard, a mouse, a touch screen, a microphone, a trackball, or the like, or a combination thereof. Exemplary output devices may include a display device, a loudspeaker, a printer, a projector, or the like, or a combination thereof. Exemplary display devices may include a liquid crystal display (LCD), a light-emitting diode (LED)-based display, a flat panel display, a curved screen, a television device, a cathode ray tube (CRT), or the like, or a combination thereof.

Merely by way of example, a user (e.g., an operator) of the processing device 140 may input data related to an object (e.g., a patient) that is being/to be imaged/scanned through the I/O 330. The data related to the object may include identification information (e.g., the name, age, gender, medical history, contract information, physical examination result, etc.) and/or the test information including the nature of the MRI scan that must be performed. The user may also input parameters needed for the operation of the MRI apparatus 110, such as image contrast and/or ratio, a region of interest (ROI), slice thickness, an imaging type (e.g., T1 weighted imaging, T2 weighted imaging, proton density weighted imaging, etc.), T1, T2, an echo type (spin echo, fast spin echo (FSE), fast recovery FSE, single shot FSE, gradient recalled echo, fast imaging with steady-state procession, and so on), a flip angle value, acquisition time (TA), echo time (TE), repetition time (TR), echo train length (ETL), the number of phases, the number of excitations (NEX), inversion time, bandwidth (e.g., RF receiver bandwidth, RF transmitter bandwidth, etc.), a scan type, a type of sampling, or the like, or any combination thereof. The I/O may also display MR images generated based on the sampled data.

The communication port 340 may be connected to a network (e.g., the network 120) to facilitate data communications. The communication port 340 may establish connections between the processing device 140 and the MRI apparatus 110, the terminal 130, or the storage device 150. The connection may be a wired connection, a wireless connection, or a combination of both that enables data transmission and reception. The wired connection may include an electrical cable, an optical cable, a telephone wire, or the like, or any combination thereof. The wireless connection may include Bluetooth, Wi-Fi, WiMax, WLAN, ZigBee, mobile network (e.g., 3G, 4G, 5G, 6G, etc.), or the like, or a combination thereof. In some embodiments, the communication port 340 may be a standardized communication port, such as RS232, RS485, etc. In some embodiments, the communication port 340 may be a specially designed communication port. For example, the communication port 340 may be designed in accordance with the digital imaging and communications in medicine (DICOM) protocol.

Figure 4:
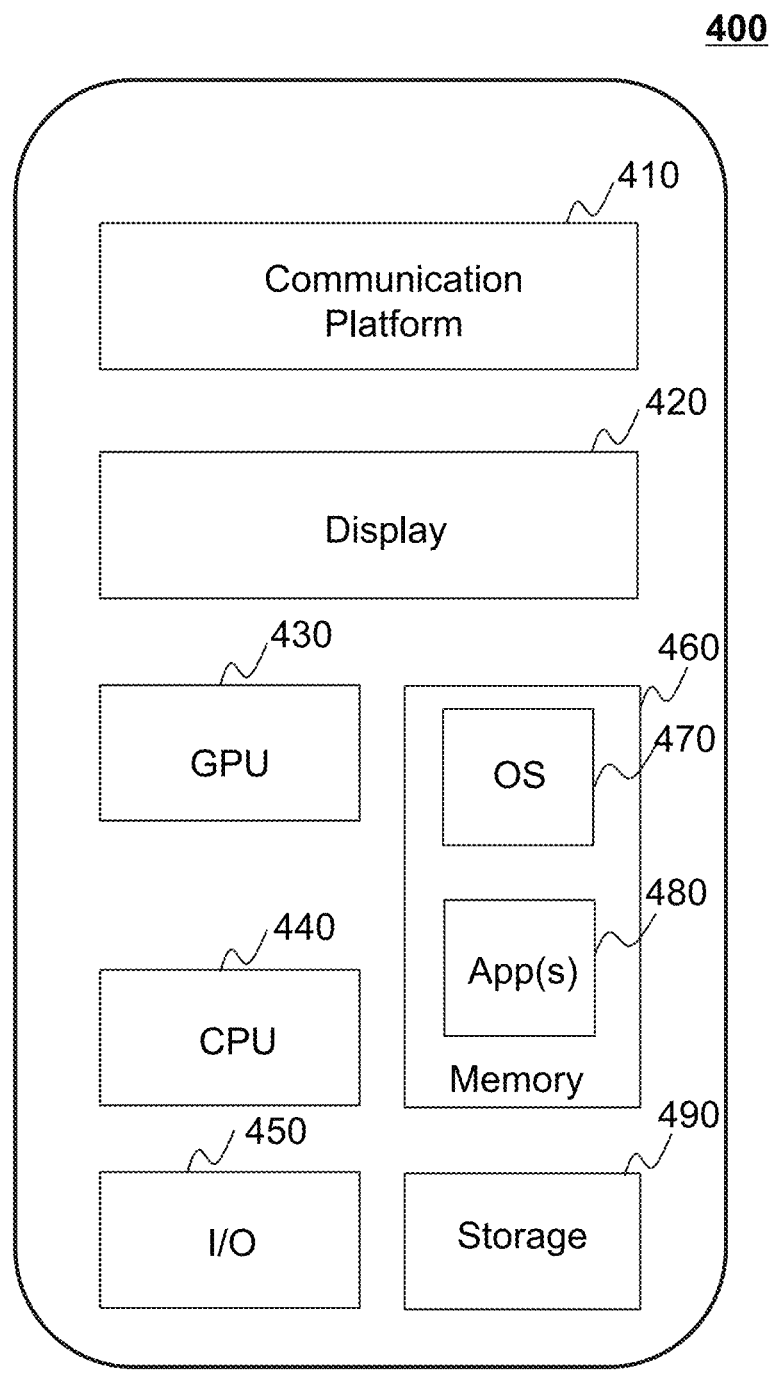
FIG. 4 is a schematic diagram illustrating exemplary hardware and/or software components of a mobile device according to some embodiments of the present disclosure.

FIG. 4 is a schematic diagram illustrating exemplary hardware and/or software components of a mobile device on which a terminal may be implemented according to some embodiments of the present disclosure. As illustrated in FIG. 4, mobile device 400 may include a communication platform 410, a display 420, a graphic processing unit (GPU) 430, a central processing unit (CPU) 440, a I/O 450, a memory 460, and a storage 490. In some embodiments, any other suitable component, including but not limited to a system bus or a controller (not shown), may also be included in the mobile device 400. In some embodiments, a mobile operating system 470 (e.g., iOS, Android, Windows Phone, HM OS, etc.) and one or more applications 480 may be loaded into the memory 460 from the storage 490 in order to be executed by the CPU 440. The applications 480 may include a browser or any other suitable mobile apps for receiving and rendering information relating to image processing or other information from the processing device 140. User interactions with the information stream may be achieved via the I/O 450 and provided to the processing device 140 and/or other components of the imaging system 100 via the network 120.

To implement various modules, units, and their functionalities described in the present disclosure, computer hardware platforms may be used as the hardware platform(s) for one or more of the elements described herein. The hardware elements, operating systems and programming languages of such computers are conventional in nature, and it is presumed that those skilled in the art are adequately familiar therewith to adapt those technologies to generate and track shapes of a target as described herein. A computer with user interface elements may be used to implement a personal computer (PC) or another type of work station or terminal device, although a computer may also act as a server if appropriately programmed. It is believed that those skilled in the art are familiar with the structure, programming and general operation of such computer equipment and as a result the drawings should be self-explanatory.

Figure 5:
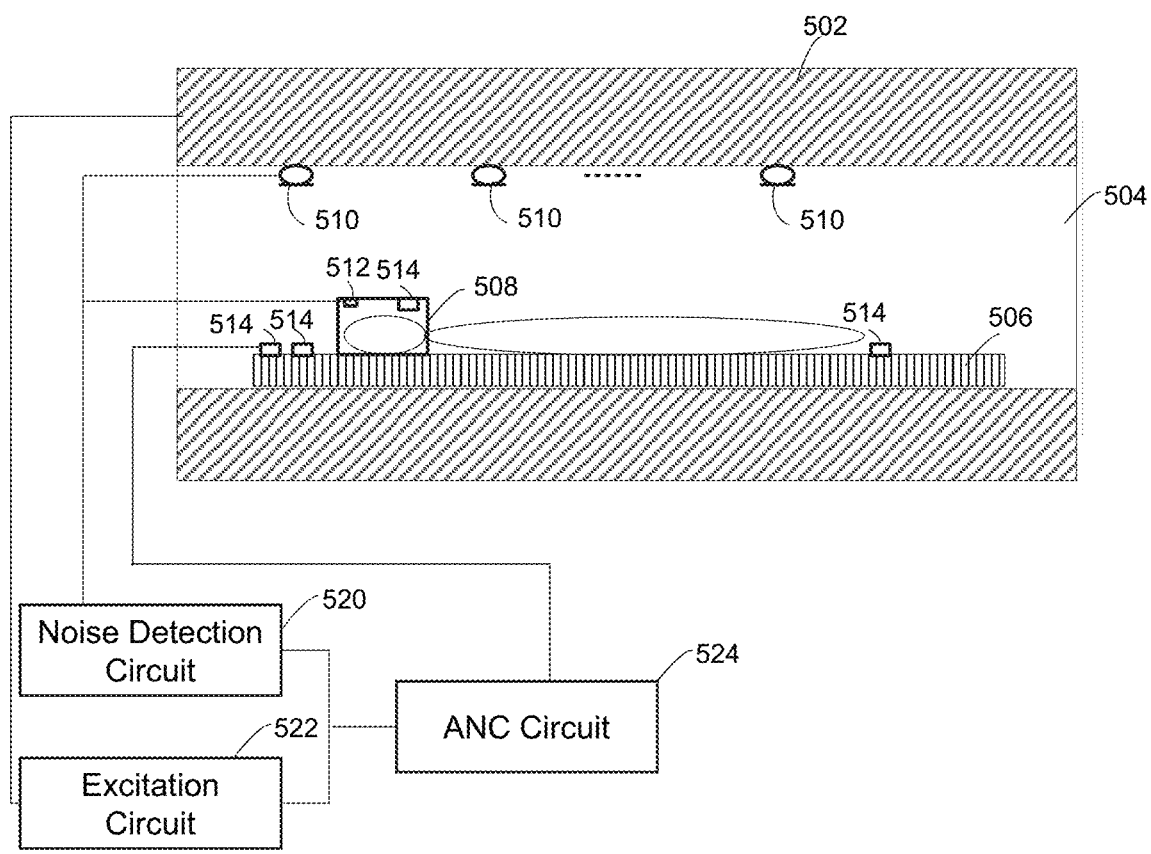
FIG. 5 is a schematic diagram illustrating an exemplary noise cancellation system (or noise reduction system) according to some embodiments of the present disclosure.

FIG. 5 is a schematic diagram illustrating an exemplary noise cancellation system (or noise reduction system) according to some embodiments of the present disclosure. The noise cancellation system may be compatible for a medical imaging apparatus (e.g., a scanning device, a treatment device) in structures and/or functionalities. It should be noted that the following description is provided with reference to exemplary embodiments that the medical imaging apparatus includes a scanning device (e.g., an MRI apparatus) unless otherwise stated. A noise cancellation system used with a treatment device may be similar to the noise cancellation system used with the scanning device, and relevant descriptions are not repeated herein. In some embodiments, noise cancellation system 500 illustrated in FIG. 5 may be implemented on the imaging system 100. In some embodiments, the noise cancellation system 500 may be regarded as a portion of the imaging system 100. In some embodiments, the noise cancellation system 500 may be provided as an add-on to any medical device (e.g., the MRI apparatus 110), providing medical device manufacturer(s) and/or users the flexibility to conveniently adopt the systems and methods as described in the present disclosure without significant changes to the design or configurations of the medical device.

The acoustic noise produced during the MRI scanning is a result of the rapidly switching electric currents that drive the pulse gradient magnetic fields. The acoustic noise can cause a serious uncomfortable feeling for the subject being scanned. In some embodiments, the noise cancellation system 500 may be configured to actively cancel the acoustic noise near (or around) a target position associated with the subject, thereby forming a regional quiet zone covering the target position (e.g., a position of the ears of the patient). The uncomfortable feeling occurred during the MRI scanning may be relieved and even avoided.

As illustrated in FIG. 5, the noise cancellation system 500 may include a first array of noise detection units 510, a second array of noise detection units 512, one or more denoising units 514, a noise detection circuit 520, and an active noise control (ANC) circuit 524. In some embodiments, at least a portion of the noise cancellation system 500 may be operably coupled or integrated to an MRI apparatus (e.g., the MRI apparatus 100). As described in connection with FIG. 2, an exemplary MRI apparatus may include a magnet assembly 502 composed of a main magnet 201 and gradient coils 202, a scanning bore 504 for accommodating the subject to be scanned, a support platform 506 for supporting the subject, and a radio frequency (RF) coil device 508 for detecting MR signals associated with the subject. In some embodiments, the MRI apparatus may further include an excitation circuit 522 for operating the gradient coils. The MRI apparatus illustrated in FIG. 5 is the same as or similar to the MRI apparatus 110. In some embodiments, the excitation circuit 522 may be accompanied with a plurality of components for generating the gradient magnetic fields (e.g., Gx, Gy, and Gz), such as waveform generator 216, X gradient amplifier 204, Y gradient amplifier 205, and Z gradient amplifier 206.

In some embodiments, the first array of noise detection units 510 may be configured to detect first noise signals inside the scanning bore 504. At least part of the first noise signals are caused by the vibration of the gradient coils during the MRI scanning. The first noise signals refer to acoustic noises within the scanning bore 504. In some embodiments, the first array of noise detection units 510 may be disposed in the scanning bore 504. For example, the first array of noise detection units 510 may be positioned to an inner surface of the scanning bore 504. In some embodiments, the first array of noise detection units 510 may be evenly set on the inner surface of the scanning bore 504 of the MRI apparatus. For example, the first array of noise detection units 510 can be spaced equally in accordance with a certain orientation (e.g., along the circumference of the inner surface). In some embodiments, the first array of noise detection units 510 may be set on the inner surface of the scanning bore 504 of the MRI apparatus irregularly. For example, at least part of the first array of noise detection units 510 can be spaced unequally in accordance with a certain orientation (e.g., along the circumference of the inner surface). In some embodiments, the first array of noise detection units 510 may include a plurality of microphones that can operate in the magnetic fields, such as non-magnetic microphones. Exemplary non-magnetic microphone includes an optical microphone, an electric capacitor microphone (ECM), a piezoelectric microphone, a micro-machined silicon (MEMS) microphone, or the like, or any combination thereof. The non-magnetic microphones can work normally regardless of the effect of magnetism of the magnetic fields.

In some embodiments, the second array of noise detection units 512 may be configured to detect second noise signals near (or around) a target position associated with the subject. As used herein, the term "near" may indicate that the second noise signals are even or steady in an area including the target position. In some embodiments, the area may be relatively small. In some embodiments, the second array of noise detection units 512 may detect second noise signals near the target position associated with the subject by detecting second noise signals at the target position. In some embodiments, the second noise signals may include error noise signals, which is the net response of the original acoustic noises (e.g., the first noise signals) and sounds produced by one or more denoising units (e.g., denoising units 514). For example, the error noise signals can be the sum of the sounds and the first noise signals arriving at the target position. In other words, the second noise signals may include a portion of the first noise signals which cannot be eliminated by the one or more denoising units. In some embodiments, the second array of noise detection units 512 may be disposed near the target position (e.g., the position of ears of the subject). In some embodiments, distance(s) between one or more of the second array of noise detection units and the target position may be properly set such that the noise at the target position can be detected accurately. For example, a first one of the second array of noise detection units 512 is disposed near the position of an ear of the subject, and a second one of the second array of noise detection units 512 is disposed near the position of the other ear of the subject. As illustrated in FIG. 5, the second array of noise detection units 512 may be fitted to the RF coil 508 and detect the second noise signals near the ears of the subject. As used herein, the RF coil 508 may be a head RF coil device. Noted that the second array of noise detection units may be arranged near the target position in various fashions. In some embodiments, the second array of noise detection units 512 may be evenly set around the target position. For example, the second array of noise detection units 512 can be spaced equally in accordance with a certain orientation (e.g., surrounding the ears of the subject). In some embodiments, the second array of noise detection units 512 may be set around the target position irregularly. For example, at least part of the second array of noise detection units 512 can be spaced unequally in accordance with a certain orientation (e.g., surrounding the ears of the subject). In some embodiments, the second array of noise detection units 512 can be similar to or same as the first array of noise detection units 510. Each of the second array of noise detection units 512 may include a non-magnetic microphone.

In some embodiments, the first noise signals detected by the first array of noise detection units 510 and the second noise signals detected by the second array of noise detection units 512 can be transmitted to the noise detection circuit 520 for further processing. In some embodiments, the noise detection circuit 520 may include a first noise detection circuit for processing the first noise signals and a second noise detection circuit for processing the second noise signals. In some embodiments, the noise detection circuit 520 can be accompanied with an amplifier, a filter and an analogue digital converter, which itself is connected to a noise detection unit (e.g., a microphone). The noise detection circuit 520 may be configured to filter the noise signals and transform the filtered noise signals into digital signals which are processed by the ANC circuit 524.

In some embodiments, the ANC circuit 524 may be configured to determine anti-noise signals based on the first noise signals, the second noise signals and excitation signals. The excitation signals are used for the operation of gradient coils of the MRI apparatus. The excitation signals can be acquired by the excitation circuit 522. In some embodiments, the excitation signals may include electrical signals associated with a pulse sequence, a section thickness, a field of view (FOV), repetition time (TR), echo time (TE), or the like, or any combination thereof. In some embodiments, the ANC circuit 524 may be operably coupled to/with a digital signal processor (e.g., the processing device 140, the processor 310). The ANC circuit 524 can be regarded as a processing circuit to determine the anti-noise signals, which have an opposite phase to the phase of the noises arriving at the target position. In some embodiments, the ANC circuit 524 may determine the anti-noise signals based on at least one of a target noise prediction model, a filtered-x least mean squares (FXLMS) algorithm based noise cancellation model, or a sound field simulation field. More descriptions regarding the determination of the anti-noise signals can be found elsewhere in the present disclosure (e.g., FIGS. 9-12, and the descriptions thereof).

In some embodiments, the one or more denoising units 514 may be configured to generate, in response to the anti-noise signals, sounds for cancelling the noises near (or around) the target position. In some embodiments, the one or more denoising units 514 may generate the sounds for cancelling the noises at the target position. In some embodiments, the denoising unit(s) 514 may include a sound generator for generate the sounds in order to counteract the noises near (or around) the target position. In some embodiments, at least one portion of the one or more denoising units 514 can be selected to generate the sounds based on acoustic properties of the anti-noise signals. The acoustic properties may include an energy of noise, an amplitude of noise, a phase of noise, a frequency of noise, or the like, or any combination thereof. In response to different energies of the anti-noise signals, specified denoising unit(s) 514 can be selected to generate the sounds for counteract the noises near (or around) the target position. For example, a first portion of the one or more denoising units 514 can be selected to generate a first sound in response to a first energy of a first anti-noise signal, while a second portion of the one or more denoising units 514 can be selected to generate a second sound in response to a second energy of a second anti-noise signal. In some embodiments, the first portion and the second portion of the one or more denoising units 514 can be different from each other. In some embodiments, the first portion and the second portion of the one or more denoising units can be overlapped partially. The selection of denoising units can facilitate to generate appropriate sound signals to cancel the noises.

In some embodiments, the one or more denoising units 514 may be fitted to the support platform 506 and near the target position (e.g., the position of the ears of the subject). For example, the distance between the one or more denoising units 514 and the target position may be properly set such that the one or more denoising units 514 may generate the sounds for cancelling the noises at the target position. In some embodiments, the one or more denoising units 514 may be fitted to a local coil (not shown in the figure) associated with the target position. In some embodiments, the one or more denoising units 514 may be fitted to an inner surface of the scanning bore of the MRI apparatus (not shown in FIG. 5). In some embodiments, the denoising unit(s) 514 may include a vibration component for vibrating the support platform 506 and/or the local coil in accordance with the anti-noise signals, thereby generating the sounds for cancelling the noises. In some embodiments, the vibration component may be a piezoelectric component that can be operated in the magnetic field. In some embodiments, the denoising unit(s) 514 may include a direction speaker configured to transmit the sounds along a certain direction towards the target position in accordance with the anti-noise signals. In some embodiments, the direction speaker can be disposed inside the scanning bore 504. In some embodiments, the direction speaker can be disposed outside of the scanning bore 504. In some embodiments, the direction speaker may include a non-magnetic speaker, such as a piezoelectric speaker. In some embodiments, the one or more denoising units 514 may be assembled instead of using conventional headset or headphone used for canceling noises. In some cases, the use of the headset or headphone can occupy the limited scanning space inside the scanning bore and disturb an imaging process. The convenient arrangements of the one or more denoising units 514 may facilitate to save the scanning space and avoid to disturb the imaging process.

Figure 6:
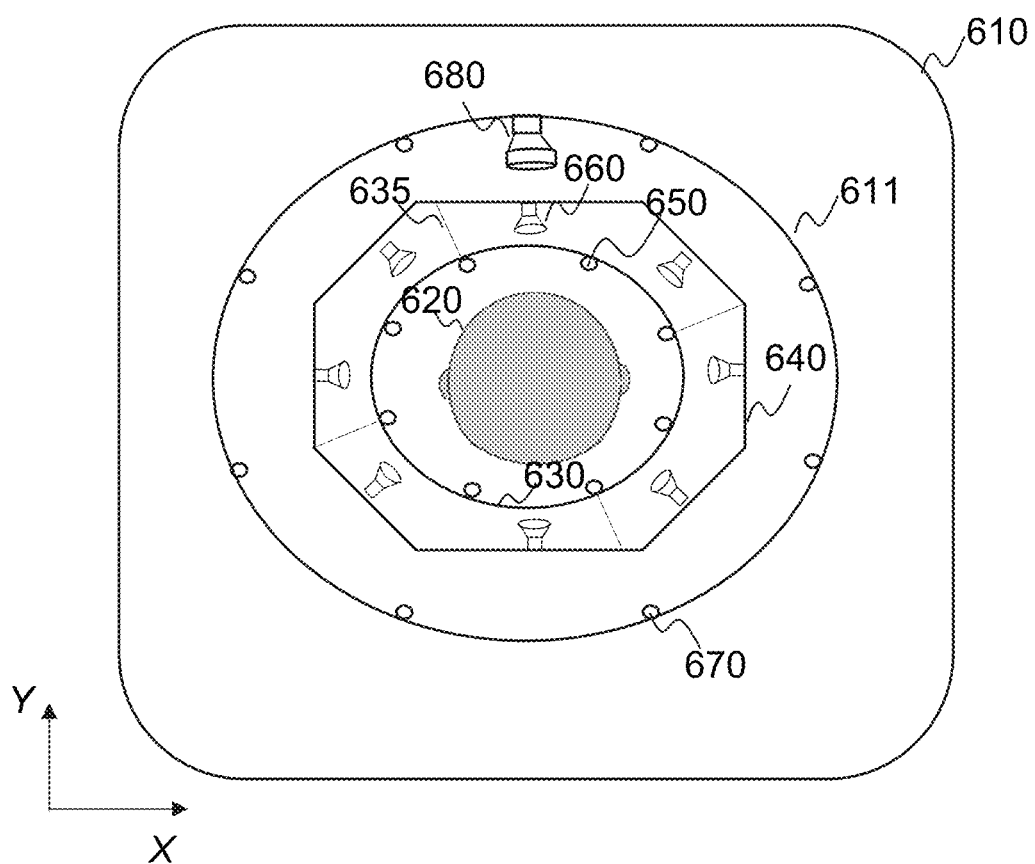
FIG. 6 is a schematic diagram of an exemplary configuration of a noise cancellation system according to some embodiments of the present disclosure.

FIG. 6 is a schematic diagram of an exemplary configuration of a noise cancellation system (e.g., the noise cancellation system 500) according to some embodiments of the present disclosure. The components of the noise cancellation system can be integrated to an MRI apparatus (e.g., the MRI apparatus 100 or the MRI apparatus illustrated in FIG. 5) and be as part of the MRI apparatus. For illustrative purpose, FIG. 6 shows a cross-sectional view of the MRI apparatus including the noise cancellation system. As illustrated in FIG. 6, the MRI apparatus may include a gantry 610 for accommodating components, such as the main magnet 201, the gradient coils 202 etc. A subject 620 may be placed in a scanning region (e.g., the scanning bore 504) of the MRI apparatus for an imaging scan. The RF coil(s) 630 may surround the head of the subject 620 for receiving MR signals associated with the head during the MRI scan. In some embodiments, the RF coil(s) 630 may include a quadrature coil. A bracket 640 is properly connected to an outer surface of the RF coil(s) 630. For example, the bracket 640 is connected to the outer surface of the RF coil(s) 630 through four connecting rods 635. The bracket 640 may have a shape of a triangle, a rectangle, a polygon, a circle, etc. Merely by way of example, the bracket 640 may have a shape of an octagon.

In some embodiments, a locating unit 680 may be equipped with the MRI apparatus. The locating unit 680 may be configured to position the target position associated with the subject 620. For example, the locating unit 680 may include a tracking sensor (e.g., an optical sensor). The locating unit 680 may be compatible with the MRI apparatus. The locating unit 680 may be positioned in the scanning bore of the MRI apparatus. For example, the locating uniting 680 may be set on an inner surface of the scanning bore. The locating uniting 680 may identify the ears of the subject, and determine the position (e.g., in the form of coordinates) of each ear. In some embodiments, the locating uniting 680 may track the ears of the patient in real time, and generate real-time coordinates of each ear.

As shown in FIG. 6, a first array of microphones 670 and a second array of microphones 650 are arranged in the scanning bore of the MRI apparatus. The first array of microphones 670 may be positioned on an inner surface of the scanning bore of the MRI apparatus. In some embodiments, the first array of microphones 670 may be evenly set on the inner surface of the scanning bore of the MRI apparatus. In some embodiments, the first array of microphones 670 may be set on the inner surface of the scanning bore of the MRI apparatus irregularly. The number or count of microphones of the first array may be set by a user, according to default settings, etc. The second array of microphones 650 may be positioned on an inner surface of the RF coil(s) 630. In some embodiments, the second array of microphones 650 may be evenly set on the inner surface of the RF coil(s) 630. In other words, intervals between each two neighboring microphones may be the same. In some embodiments, the second array of microphones 650 may be set on the inner surface of the RF coil(s) 630 irregularly. In other words, intervals between each two neighboring microphones may vary, for example, according to actual needs. The number or count of microphones of the second array may be set by a user, according to default settings, etc.

When the MRI apparatus scans the subject, the gradient coils wrapped in epoxy resin may vibrate due to the Lorentz force enforced on the gradient coils in the magnetic field, thus producing noises in the scanning region. The two arrays of microphones 650 and 670 may detect noise signals, respectively. For example, the first array of microphones 670 can be configured to detect the first noise signals inside the scanning bore, which result from the vibration caused by the operation of gradient coils. The second array of microphones 650 can be configured to detect the second noise signals near (or around) the target position. The second noise signals may include error noise signals, which is the net response of the original acoustic noises (e.g., the first noise signals) and sounds produced by an array of denoising units 660. In some embodiments, a noise distribution (or a noise field) inside the scanning bore may be determined based on noise signals detected by the first array and the second array of microphones. For example, a sound field simulation model can be constructed to model the noise field within the scanning bore. The sound field simulation model may simulate the components of the MRI apparatus including the noise cancellation system based on, such as a finite element simulation of the sound field distribution. In some embodiments, the sound field simulation model can be constructed by one or more commercial simulation tools (e.g., MATLAB, COMSOL Monte-Carlo simulation, etc.). In some embodiments, the sound field simulation model can be embodied in a digital signal processor (DSP), such as the ANC circuit 524. Further the noise level of noises arriving at the target position can be determined based on the sound field simulation model. The noise level can be indicated by acoustic properties of noise, such as an energy of noise, an amplitude of noise, a phase of noise, a frequency of noise, etc.

As illustrated in FIG. 6, the array of denoising units 660 may be set on an inner surface of the bracket 640. For example, the array of denoising units 660 may include piezoelectric components. The piezoelectric component can be used to vibrate the bracket 640 in order to generate sounds for cancelling the noises around the target position. As another example, the array of denoising units 660 may include non-magnetic speakers. The non-magnetic speakers can be used to generate directional sounds for cancelling the noises around the target position. In some embodiments, the array of denoising units 660 may be evenly set on the inner surface of the bracket 640. In some embodiments, the array of denoising units 660 may be set on the inner surface of the bracket 640 irregularly. The number or count of the denoising units may be set by a user, according to actual needs, etc.

The array of denoising units 660 may produce sounds having particular acoustic properties at the target position (e.g., the position of each ear of the subject). For example, the sounds produced by the array of denoising units 660 at the position of each ear may have the same amplitude as the amplitude of the noises arriving at the position of the corresponding ear, the same frequency as the frequency of the noises arriving at the position of the corresponding ear, and an opposite phase (i.e., having a difference of $\pi$) relative to the phase of the noises arriving at the position of the corresponding ear. Since the phase of the sounds produced by the array of denoising units 660 at the position of each ear is opposite to the phase of the noises arriving at the position of the corresponding ear, the noises arriving at the position of each ear may be counteracted by the sounds produced by the array of denoising units 660, thus reducing or cancelling the noises heard by the subject.

Figure 7:
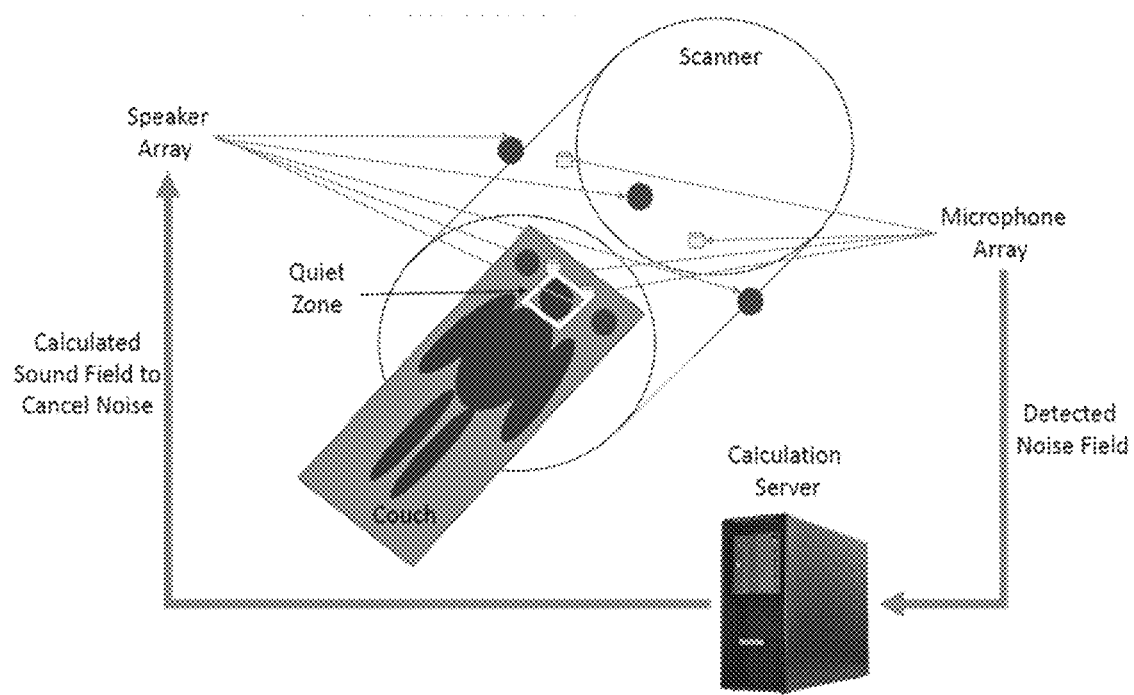
FIG. 7 is a schematic diagram illustrating an exemplary noise cancellation system according to some embodiments of the present disclosure.

FIG. 7 is a schematic diagram illustrating an exemplary noise cancellation system according to some embodiments of the present disclosure. The noise cancellation system 700 may be implemented to a medical imaging apparatus (e.g., an MRI apparatus, or an MRI scanner). As illustrated in FIG. 7, the microphone array may include a first array of microphones (e.g., 510 or 670) and a second array of microphones (e.g., 512 or 650). The first array of microphones may be positioned to the inner surface of the scanning bore of the scanner. In some embodiments, the first array of microphones may be configured to detect first noise signals inside the scanning bore. The first noise signals can be acoustic noises caused by the vibration of gradient coils during the MRI scanning. In some embodiments, the second array of microphones may be positioned to near (or around) the target position associated with the subject. For example, the target position is a position of ears of the subject placed on the couch (e.g., the support platform 506). The second array of microphones may be configured to detect second noise signals near (or around) the target position (e.g., the position of the ears). In some embodiments, the second noise signals may correlate with the first noise signals and sounds produced by an array of speaker (also referred to as speaker array). The second noise signals may include error noise signals. The error signals can be the sum of the sounds and the first noise signals arriving at the target position. In some embodiments, a sound field simulation model can be applied to detect or determine a noise field inside the scanning bore based on information associated with the first noise signals and the second noise signals. In some embodiments, a server (e.g., the processing device 140 or the processor 310) may calculate a noise level at the target position from the noise field. The server may determine, based on the noise level, a sound field indicative of anti-noise signals. The determined sound field can be used to cancel the noises arriving at the target position. In accordance with the sound field, the speaker array can generate the sounds to cancel the noises arriving at the target position. Thus, a regional quite zone near the target position can be formed. In some embodiments, the microphone array and the speaker array may be in compatible with the magnetic field required for image scanning. For example, the microphone array may include one or more non-magnetic microphones (e.g., piezoelectric microphones). The speaker array may include one or more non-magnetic speakers (e.g., piezoelectric speakers). In some embodiments, the speaker array may be replaced by vibration components. The vibration components may generate the sounds by vibrating the support platform (e.g., the couch) near the target position. As described in connection with FIG. 7, the microphone array and the speaker array may be assembled in the scanner instead of using conventional headset or headphone used for canceling noises, which may facilitate to save the limited scanning space and avoid to disturb an imaging process.

Figure 8:
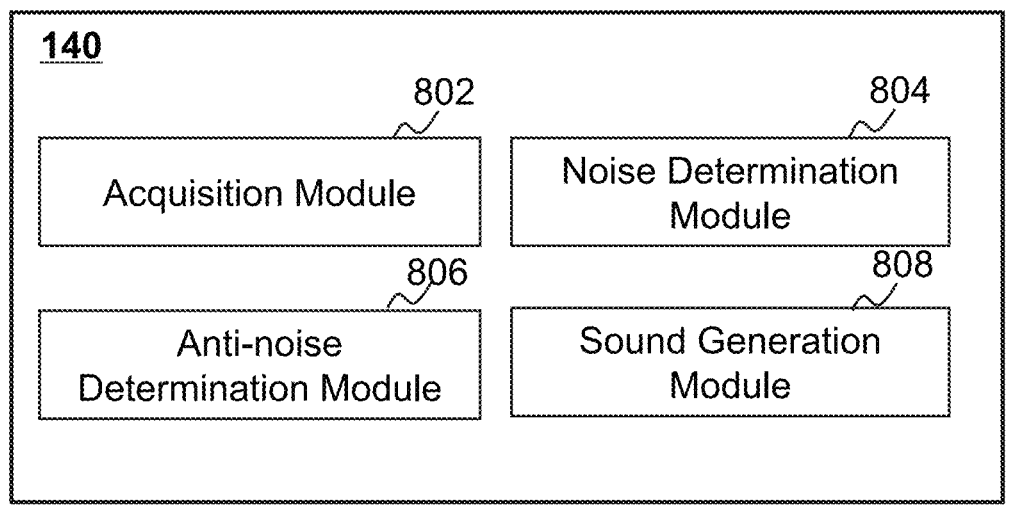
FIG. 8 is a block diagram illustrating an exemplary processing device according to some embodiments of the present disclosure.

FIG. 8 is a block diagram illustrating an exemplary processing device according to some embodiments of the present disclosure. In some embodiments, the processing device 140 may be implemented on a computing device 300 (e.g., the processor 310) illustrated in FIG. 2 or a CPU 440 illustrated in FIG. 4. As illustrated in FIG. 8, the processing device 140 may include an acquisition module 502, a noise determination module 504, an anti-noise determination module 506 and a sound generation module 508. Each of the modules described above may be a hardware circuit that is designed to perform certain actions, e.g., according to a set of instructions stored in one or more storage media, and/or any combination of the hardware circuit and the one or more storage media.

In some embodiments, the acquisition module 802 may acquire first noise signals by a first array of noise detection units disposed in a scanning bore (e.g., the scanning bore 504). The first array of noise detection units may be configured to detect the first noise signals (i.e., acoustic noises) inside the scanning bore. In some embodiments, the first noise signals may be caused by the vibration of gradient coils (e.g., the gradient coils 202) during the MRI scanning. In some embodiments, the first array of noise detection units may be arranged inside the scanning bore in various fashions, as illustrated in FIG. 5 or FIG. 6.

In some embodiments, the acquisition module 802 may acquire second noise signals by a second array of noise detection units near a target position associated with a subject. The second array of noise units may be configured to detect the second noise signals near (or around) the target position associated with the subject. In some embodiments, the second noise signals may include error noise signals, which is the net response of the original acoustic noises (e.g., the first noise signals) and sounds produced by one or more denoising units. For example, the error signals can be the sum of the sounds and the first noise signals arriving at the target position. In some embodiments, the second noise signals may include a portion of the first noise signals which cannot be eliminated by the one or more denoising units. In some embodiments, the second array of noise detection units may be arranged near (or around) the target position in various fashions. In some embodiments, the second array of noise detection units may be evenly set around the target position. For example, the second array of noise detection units can be spaced equally in accordance with a certain orientation (e.g., surrounding the ears of the subject). In some embodiments, the second array of noise detection units may be set around the target position irregularly. For example, at least part of the second array of noise detection units can be spaced unequally in accordance with a certain orientation (e.g., surrounding the ears of the subject).

In some embodiments, the acquisition module 802 may obtain excitation signals used for the operation of the gradient coils. As described in connection with FIG. 6, the excitation circuit 522 may be configured to generate the excitation signals. The excitation circuit 522 may be accompanied with the components for generating the gradient magnetic fields, such as waveform generator 216, X gradient amplifier 204, Y gradient amplifier 205, Z gradient amplifier 206, etc. The excitation signals may include electrical signals associated with a pulse sequence, a section thickness, a field of view (FOV), repetition time (TR), echo time (TE), or the like, or any combination thereof. In some embodiments, the processing device may obtain the excitation signals through the excitation circuit 522.

In some embodiments, the noise determination module 804 may determine predicted noise signals near the target position by feeding first noise signals, second noise signals and excitation noise signals to the target noise prediction model. The predicted noise signals may be used to measure a noise distribution (or a noise field) of the noises arriving at the target position. In some embodiments, the target noise prediction model may be determined by training a preliminary machine learning model based on multiple groups of training data using a model training algorithm. Exemplary model training algorithms may include a gradient descent algorithm, a Newton's algorithm, a Quasi-Newton algorithm, a Levenberg-Marquardt algorithm, a conjugate gradient algorithm, or the like, or a combination thereof. The multiple groups of training data (also referred to as training set) may include historical first noise signals, historical second noise signals and historical excitation signals sampled from historical operations of the gradient coils. In some embodiments, the machine learning model may be constructed based on at least one of a convolutional machine learning model (CNN), a fully convolutional neural network (FCN) model, a generative adversarial network (GAN), a back propagation (BP) machine learning model, a radial basis function (RBF) machine learning model, a deep belief nets (DBN) machine learning model, an Elman machine learning model, or the like, or a combination thereof.

In some embodiments, the noise determination module 804 may determine, based on first noise signals and second noise signals, a noise level at the target position with the sound field simulation model. The noise level can be indicated by acoustic properties of noises arriving at the target position, such as an energy of noise, an amplitude of noise, a phase of noise, a frequency of noise, etc. The noise level of the noises arriving at the target position may be determined according to the simulation of noise distribution output by the sound field simulation model.

In some embodiments, the anti-noise determination module 806 may be configured to determine anti-noise signals based on the predicted noise signals. In some embodiments, the anti-noise determination module 806 may obtain acoustic properties of the predicted noise signals, such as an energy, an amplitude, a phase, a frequency, etc. The anti-noise determination module 806 may determine the anti-noise signals based on the obtained acoustic properties. The determined anti-noise signals may have an opposite phase to the phase of the predicted noise signals, while have the same amplitude and/or the same frequency relative to the predicted noise signals.

In some embodiments, the anti-noise determination module 806 may be configured to designate the first noise signals and the excitation signals as feedforward input signals of an FXLMS algorithm based noise cancellation model, and designate the second noise signals as feedback input signals of the FXLMS algorithm based noise cancellation model. The anti-noise determination module 806 may determine, based on the FXLMS algorithm based noise cancellation model, the anti-noise signals by minimizing the second noise signals (i.e., the error noise signals). The FXLMS algorithm based noise cancellation model can be described in connection with FIG. 11B.

In some embodiments, the anti-noise determination module 806 may determine the anti-noise signals based on the noise level. In some embodiments, the anti-noise determination module 806 may analyze the acoustic properties indicative of the noise level, and determine the anti-noise signals based on the acoustic properties. The determined anti-noise signals may have an opposite phase to the phase of the noises arriving at the target position, while have the same amplitude and/or the same frequency relative to the noises arriving at the target position.

In some embodiments, the sound generation module 810 may generate, via the one or more denoising units, sounds in response to the anti-noise signals. As a response, the generated sounds may have particular acoustic properties at the target position. For example, the sounds at the position of each ear may have the same amplitude as the amplitude of the noises arriving at the position of the corresponding ear, the same frequency as the frequency of the noises arriving at the position of the corresponding ear, and an opposite phase (i.e., having a difference of $\pi$) relative to the phase of the noises arriving at the position of the corresponding ear. Since the phase of the sounds at the position of each ear is opposite to the phase of the noises arriving at the position of the corresponding ear, the noises arriving at the position of each ear may be counteracted by the sounds, thus reducing or cancelling the noises heard by the subject. A regional quiet zone covering the target position may be formed accordingly.

In some embodiments, a plurality of denoising parameters corresponding to the anti-noise signals may be determined. The plurality of denoising parameters may be used to direct one or more denoising units to generate sounds for cancelling the noises arriving at the target position. In some embodiments, the plurality of denoising parameters may include electrical properties (e.g., a current, a voltage, a frequency, etc.) of a current input into each of the one or more denoising units.

Figure 9:
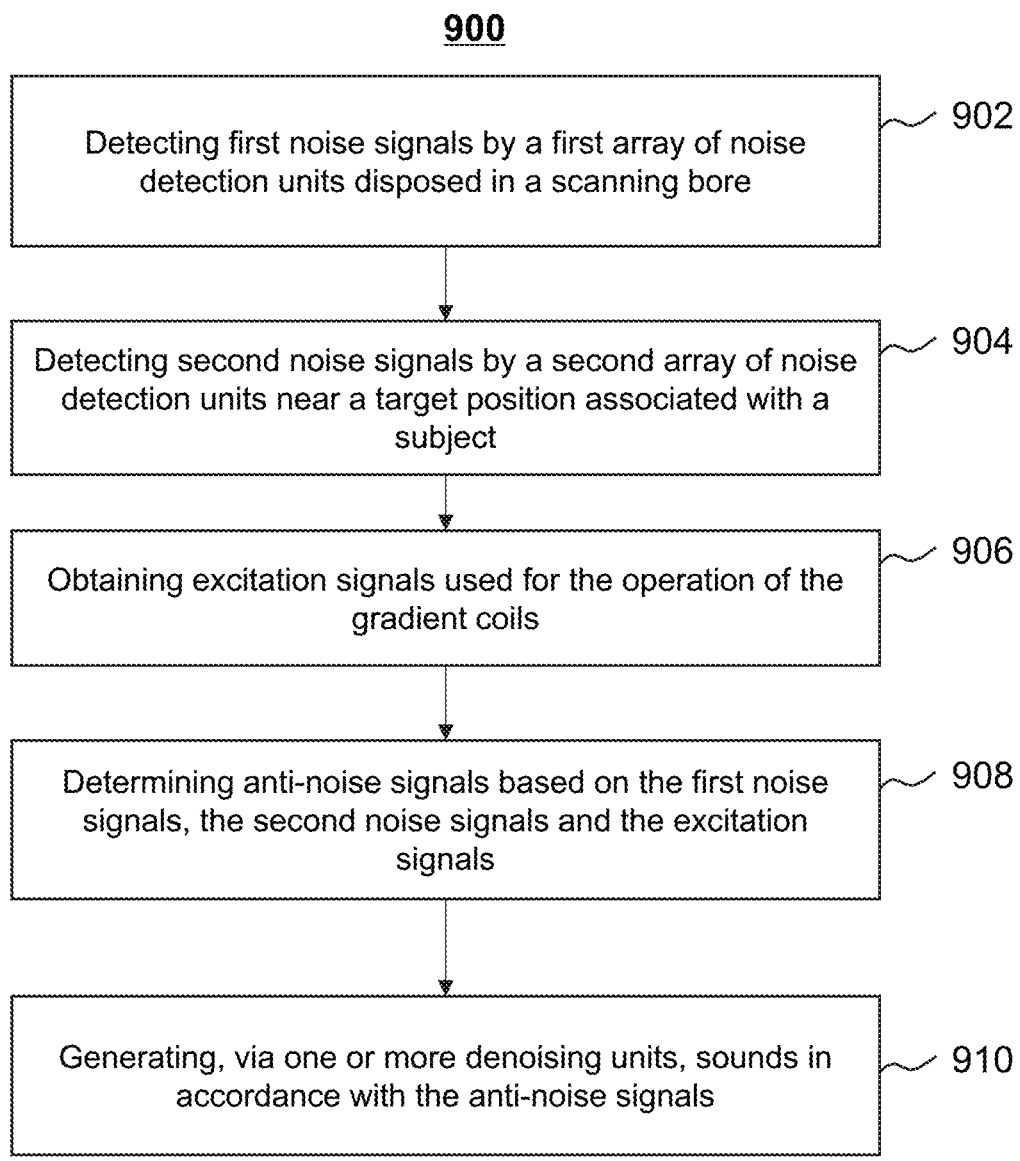
FIG. 9 is a flowchart illustrating an exemplary process of an active noises control (ANC) in a medical imaging apparatus according to some embodiments of the present disclosure.

FIG. 9 is a flowchart illustrating an exemplary process of an active noises control (ANC) in a medical imaging apparatus (e.g., an MRI apparatus 110) according to some embodiments of the present disclosure. In some embodiments, process 900 may be implemented in the imaging system 100 illustrated in FIG. 1. For example, the process 900 may be stored in a storage device (e.g., the storage device 150, or the storage 320 of the processing device 140) as a form of instructions, and can be invoked and/or executed by the processing device 140 (e.g., the processor 310 of the processing device 140, one or more processing circuits illustrated in FIG. 5, or one or more modules in the processing device 140 illustrated in FIG. 8). The operations of the illustrated process 900 presented below are intended to be illustrative. In some embodiments, the process 900 may be accomplished with one or more additional operations not described, and/or without one or more of the operations discussed. Additionally, the order in which the operations of the process 900 as illustrated in FIG. 9 and described below is not intended to be limiting.

In 902, the processing device (e.g., the acquisition module 802 of the processing device 140 or the noise detection circuit 520) may detect first noise signals by a first array of noise detection units disposed in a scanning bore (e.g., the scanning bore 504).

The first array of noise detection units may be configured to detect the first noise signals (i.e., acoustic noises) inside the scanning bore. In some embodiments, the first noise signals may be caused by the vibration of gradient coils (e.g., the gradient coils 202) during the MRI scanning. In some embodiments, the first array of noise detection units may be arranged inside the scanning bore in various fashions. Merely for illustration, as illustrated in FIG. 5 or FIG. 6, the first array of noise detection units (510 or 670) may be positioned to an inner surface of the scanning bore. In some embodiments, the first array of noise detection units may be evenly set on the inner surface of the scanning bore of the MRI apparatus. For example, the first array of noise detection units can be spaced equally in accordance with a certain orientation (e.g., along the circumference of the inner surface). In some embodiments, the first array of noise detection units may be set on the inner surface of the scanning bore of the MRI apparatus irregularly. For example, at least part of the first array of noise detection units can be spaced unequally in accordance with a certain orientation (e.g., along the circumference of the inner surface). In some embodiments, the first array of noise detection units may include a plurality of microphones that can operate in the magnetic fields, such as non-magnetic microphones. Exemplary non-magnetic microphone includes an optical microphone, an electric capacitor microphone (ECM), a piezoelectric microphone, a micro-machined silicon (MEMS) microphone, or the like, or any combination thereof. The non-magnetic microphones can work normally regardless of the effect of magnetism of the magnetic fields. In some embodiments, the processing device may obtain the first noise signals through a first noise detection circuit (e.g., a first one of the noise detection circuit 520) connected to each of the first array of noise detection units.

In 904, the processing device (e.g., the acquisition module 802 of the processing device 140 or the noise detection circuit 520) may detect second noise signals by a second array of noise detection units near a target position associated with a subject.

The second array of noise units may be configured to detect the second noise signals near (or around) the target position associated with the subject. In some embodiments, the second noise signals may include error noise signals, which is the net response of the original acoustic noises (e.g., the first noise signals) and sounds produced by one or more denoising units. For example, the error signals can be the sum of the sounds and the first noise signals arriving at the target position. In some embodiments, the second noise signals may include a portion of the first noise signals which cannot be eliminated by the one or more denoising units.

In some embodiments, the target position associated with the subject can refer to a position of a target portion of the subject. The target portion of the subject may include a specific portion of a body of the subject, such as the head, the thorax, the upper body, or the like, or a combination thereof. In some embodiments, the target portion of the subject may include a specific organ, such as ears, eyes, the heart, etc. As used herein, the at least one target portion may be ears of the subject. In some embodiments, the target position can be determined by a locating unit (e.g., the locating unit 680) coupled with the MRI apparatus.

In some embodiments, the second array of noise detection units may be disposed near the target position (e.g., the position of ears of the subject). For example, a first one of the second array of noise detection units is disposed near the position of an ear of the subject, and a second one of the second array of noise detection units is disposed near the position of the other ear of the subject. As illustrated in FIG. 5 or FIG. 6, the second array of noise detection units (e.g., 512 or 650) may be disposed in a local radio frequency (RF) coil device, such as a head RF coil device, and detect the second noise signals near (or around) the ears of the subject.

Noted that the second array of noise detection units may be arranged near (or around) the target position in various fashions. In some embodiments, the second array of noise detection units may be evenly set around the target position. For example, the second array of noise detection units can be spaced equally in accordance with a certain orientation (e.g., surrounding the ears of the subject). In some embodiments, the second array of noise detection units may be set around the target position irregularly. For example, at least part of the second array of noise detection units can be spaced unequally in accordance with a certain orientation (e.g., surrounding the ears of the subject). In some embodiments, the second array of noise detection units can be similar to or same as the first array of noise detection units. Each of the second array of noise detection units may include a non-magnetic microphone. In some embodiments, the processing device may obtain the second noise signals through a second noise detection circuit (e.g., a second one of the noise detection circuit 520) connected to each of the second array of noise detection units.

In 906, the processing device (e.g., the acquisition module 802 of the processing device 140 or the excitation circuit 522) may obtain excitation signals used for the operation of the gradient coils.

As described in connection with FIG. 6, the excitation circuit 522 may be configured to generate the excitation signals. The excitation circuit 522 may be accompanied with the components for generating the gradient magnetic fields, such as waveform generator 216, X gradient amplifier 204, Y gradient amplifier 205, Z gradient amplifier 206, etc. The excitation signals may include electrical signals associated with a pulse sequence, a section thickness, a field of view (FOV), repetition time (TR), echo time (TE), or the like, or any combination thereof. In some embodiments, the processing device may obtain the excitation signals through the excitation circuit 522.

In 908, the processing device (e.g., the anti-noise determination module 806 of the processing device 140 or the ANC circuit 524) may determine anti-noise signals based on the first noise signals, the second signals and the excitation signals.

In some embodiments, the anti-noise signals can be determined by feeding the first noise signals, the second noise signals and the excitation signals to a target noise prediction model. The target noise prediction model may be used to determine predicted noise signals near (or around) the target position. The predicted noise signals may be used to measure a noise distribution (or a noise field) of noises arriving at the target position. The anti-noise signals may be determined based on the predicted noise signals. The anti-noise signals may have an opposite phase and the same amplitude relative to the predicted noise signals. In some embodiments, the target noise prediction model may include a machine learning model. In some embodiments, the machine learning model may be constructed based on a deep learning neural network model. Exemplary deep learning neural network models may include a convolutional machine learning model (CNN), a fully convolutional neural network (FCN) model, a generative adversarial network (GAN), a back propagation (BP) machine learning model, a radial basis function (RBF) machine learning model, a deep belief nets (DBN), an Elman machine learning model, or the like, or a combination thereof. In some embodiments, the target noise prediction model may be determined by training a preliminary machine learning model using multiple groups of training data. Each group of the multiple groups pf training data may include historical first noise signals, historical second noise signals and historical excitation signals sampled from historical operations of the gradient coils. More descriptions regarding the determination of the target noise prediction model may be found elsewhere in the present disclosure (e.g., FIG. 10 and the descriptions thereof).

In some embodiments, the anti-noise signals may be determined based on an FXLMS algorithm based noise cancellation model. The first noise signals and the excitation signals can be taken as feedforward inputs of the FXLMS algorithm based noise cancellation model. The second noise signals can be taken as feedback input of the FXLMS algorithm based noise cancellation model. The anti-noise signals may determined by minimizing the feedback (e.g., the second noise signals or the error noise signals) with the FXLMS algorithm based noise cancellation model. More descriptions of the FXLMS algorithm based noise cancellation model can be found elsewhere in the present disclosure (e.g., FIGS. 11A-11B, and the descriptions thereof).

In some embodiments, the anti-noise signals may be determined based on a sound field simulation model. The sound field simulation model may be used to determine a noise field inside the scanning bore based on the first noise signals and the second noise signals. The sound field simulation model may simulate the components of the MRI apparatus including the noise cancellation system based on, such as a finite element simulation of the sound field distribution. In some embodiments, the sound field simulation model can be constructed by one or more commercial simulation tools (e.g., MATLAB, COMSOL Monte-Carlo simulation, etc.). Further the noise level at the target position can be determined based on the sound field simulation model. The noise level can be indicated by acoustic properties of noise, such as an energy of noise, an amplitude of noise, a phase of noise, a frequency of noise, etc. The anti-noise signals may be determined based on the noise level. More descriptions regarding the sound field simulation model can be found elsewhere in the present disclosure (e.g., FIGS. 11A-11B, and the descriptions thereof).

In 910, the processing device (e.g., the sound generation module 808 of the processing device 140) may generate, via one or more denoising units, sounds in accordance with the anti-noise signals.

In some embodiments, the processing device may direct the one or more denoising units to generate the sounds in response to the anti-noise signals. As a response, the generated sounds may have particular acoustic properties at the target position. For example, the sounds at the position of each ear may have the same amplitude as the amplitude of the noises arriving at the position of the corresponding ear, the same frequency as the frequency of the noises arriving at the position of the corresponding ear, and an opposite phase (i.e., having a difference of $\pi$) relative to the phase of the noises arriving at the position of the corresponding ear. Since the phase of the sounds at the position of each ear is opposite to the phase of the noises arriving at the position of the corresponding ear, the noises arriving at the position of each ear may be counteracted by the sounds, thus reducing or cancelling the noises heard by the subject. A regional quiet zone covering the target position may be formed accordingly.

In some embodiments, a plurality of denoising parameters corresponding to the anti-noise signals may be determined. The plurality of denoising parameters may be used to direct one or more denoising units to generate sounds for cancelling the noises arriving at the target position. In some embodiments, the plurality of denoising parameters may include electrical properties (e.g., a current, a voltage, a frequency, etc.) of a current input into each of the one or more denoising units.

In some embodiments, all or a portion of the one or more denoising units can be selected to generate the sounds based on properties of the anti-noise signals (e.g., the energy, the phase, the frequency, the amplitude, etc.). In response to different energies of the anti-noise signals, specified denoising unit(s) can be selected to generate the sounds for counteracting the noises near (or around) the target position. For example, the processing device 140 may select a first portion of the one or more denoising units 514 to generate a first sound in response to a first energy of a first anti-noise signal. The processing device 140 may select a second portion of the one or more denoising units 514 to generate a second sound in response to a second energy of a second anti-noise signal. In some embodiments, the first portion and the second portion of the one or more denoising units 514 can be different from each other. In some embodiments, the first portion and the second portion of the one or more denoising units can be overlapped partially.

As described in connection with FIG. 5, in some embodiments, the one or more denoising units 514 may be fitted to the support platform 506 and near the target position (e.g., the ears of the subject). In some embodiments, the one or more denoising units 514 may be fitted to the local coil associated with the target position. In some embodiments, the denoising unit(s) 514 may include a vibration component for vibrating the support platform 506 in accordance with the anti-noise signals, thereby generating the sounds. The vibration component may be a piezoelectric component that can be operated in the magnetic field. In some embodiments, the denoising unit(s) 514 may include a direction speaker configured to transmit the sounds along a certain direction towards the target position in accordance with the anti-noise signals. In some embodiments, the direction speaker can be disposed inside the scanning bore 504. In some embodiments, the direction speaker can be disposed outside of the scanning bore 504. In some embodiments, the direction speaker may include a non-magnetic speaker, such as a piezoelectric speaker.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 908 and 910 may be integrated into a single operation.

Figure 10:
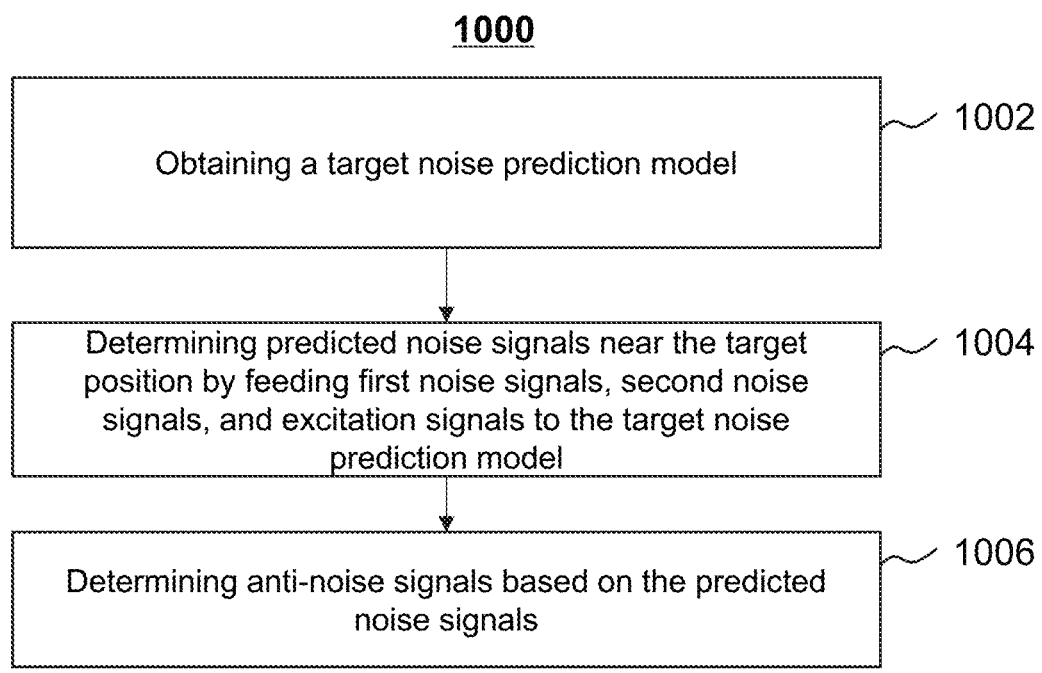
FIG. 10 is a flowchart illustrating an exemplary process for determining anti-noise signals according to some embodiments of the present disclosure.

FIG. 10 is a flowchart illustrating an exemplary process for determining anti-noise signals according to some embodiments of the present disclosure. In some embodiments, process 1000 may be implemented in the imaging system 100 illustrated in FIG. 1. For example, the process 1000 may be stored in a storage device (e.g., the storage device 150, or the storage 320 of the processing device 140) as a form of instructions, and can be invoked and/or executed by the processing device 140 (e.g., the processor 310 of the processing device 140, one or more processing circuits illustrated in FIG. 5, or one or more modules in the processing device 140 illustrated in FIG. 8). The operations of the illustrated process 1000 presented below are intended to be illustrative. In some embodiments, the process 1000 may be accomplished with one or more additional operations not described, and/or without one or more of the operations discussed. Additionally, the order in which the operations of the process 1000 as illustrated in FIG. 10 and described below is not intended to be limiting.

In 1002, the processing device (e.g., the acquisition module 802 of the processing device 140 or the ANC circuit 524) may obtain a target noise prediction model. For example, the target noise prediction model may be obtained from a storage device (e.g., the storage device 150). The target noise prediction model may be configured to predict noise signals near (or around) a target position associated with a subject (e.g., a position of the ears of the subject). The predicted noise signals may be used to measure a noise distribution (or a noise field) of the noises arriving at the target position.

The target noise prediction model may be determined by training a preliminary machine learning model based on multiple groups of training data using a model training algorithm. Exemplary model training algorithms may include a gradient descent algorithm, a Newton's algorithm, a Quasi-Newton algorithm, a Levenberg-Marquardt algorithm, a conjugate gradient algorithm, or the like, or a combination thereof. The multiple groups of training data (also referred to as training set) may include historical first noise signals, historical second noise signals and historical excitation signals sampled from historical operations of the gradient coils. In some embodiments, the training data may be collected from historical scan operations. In some embodiments, the machine learning model may be constructed based on at least one of a convolutional machine learning model (CNN), a fully convolutional neural network (FCN) model, a generative adversarial network (GAN), a back propagation (BP) machine learning model, a radial basis function (RBF) machine learning model, a deep belief nets (DBN) machine learning model, an Elman machine learning model, or the like, or a combination thereof. In some embodiments, the machine learning model may include multiple layers, for example, an input layer, multiple hidden layers, and an output layer. The multiple hidden layers may include one or more convolutional layers, one or more pooling layers, one or more batch normalization layers, one or more activation layers, one or more fully connected layers, a cost function layer, etc. Each of the multiple layers may include a plurality of nodes.

In some embodiments, the machine learning model may be trained by performing a plurality of iterations based on a cost function. Before the plurality of iterations, the plurality of learning parameters of the machine learning model may be initialized. For example, the connected weights and/or the bias vector of nodes of the machine learning model may be initialized to be random values in a range, e.g., the range from −1 to 1. As another example, all the connected weights of the machine learning model may have a same value in the range from −1 to 1, for example, 0. As still an example, the bias vector of nodes in the machine learning model may be initialized to be random values in a range from 0 to 1. In some embodiments, the plurality of learning parameters of the machine learning model may be initialized based on a Gaussian random algorithm, a Xavier algorithm, etc. Then the plurality of iterations may be performed to update the plurality of learning parameters of the machine learning model until a condition is satisfied. The condition may provide an indication of whether the machine learning model is sufficiently trained. For example, the condition may be satisfied if the value of the cost function associated with the machine learning model is minimal or smaller than a threshold (e.g., a constant). As another example, the condition may be satisfied if the value of the cost function converges. The convergence may be deemed to have occurred if the variation of the values of the cost function in two or more consecutive iterations is smaller than a threshold (e.g., a constant). As still an example, the condition may be satisfied when a specified number of iterations are performed in the training process. In some embodiments, the trained machine learning model may be validated based on multiple groups of validation data (also referred to as validation set). Similar to the training data, the validation data may also include historical first noise signals, historical second noise signals and historical excitation signals sampled from historical operations of the gradient coils. The validation data may be different from the training data. In some embodiments, the multiple groups of validation data and the multiple groups of training data may belong to a same data set. For example, 70% of the data set may be the multiple groups of training data, and 20% of the data set may be the multiple groups of validation data. In some embodiments, the target machine learning model (i.e., the target noise prediction model) may be determined by adjusting the trained machine learning model using the multiple groups of validation data. The trained machine learning model may be adjusted by adjusting the plurality of architecture parameters based on the validation set if the trained machine learning model is underfitting or overfitting; otherwise, the trained machine learning model determined may be designated as the target machine learning model.

In 1004, the processing device (e.g., the noise determination module 804 of the processing device 140 or the ANC circuit 524) may determine predicted noise signals near the target position by feeding first noise signals, second noise signals, and excitation noise signals to the target noise prediction model.

In some embodiments, the first noise signals may be detected by a first array of noise detection units disposed inside a scanning bore of a medical imaging apparatus (e.g., an MRI apparatus 110). In some embodiments, the first noise signals may be acoustic noises caused by the vibration of gradient coils during the MRI scanning. In some embodiments, the second noise signals may be detected by a second array of noise detection units near the target position. In some embodiments, the second noise signals may include error noise signals, which is the net response of the original acoustic noises (e.g., the first noise signals) and sounds produced by one or more denoising units. For example, the error noise signals can be the sum of the sounds and the first noise signals arriving at the target position. In some embodiments, the second noise signals may include a portion of the first noise signals which cannot be eliminated by the one or more denoising units. In some embodiments, excitation signals used for the operation of the gradient coils may be obtained from an excitation circuit (e.g., the excitation circuit 522). The excitation signals may include electrical signals associated with a pulse sequence, a section thickness, a field of view (FOV), repetition time (TR), echo time (TE), or the like, or any combination thereof.

The processing device may input the first noise signals, the second noise signals and the excitation signals to the target noise prediction model. The target noise prediction model may output the predicted noise signals near the target position. In some embodiments, the predicted noise signals may be used to measure a noise distribution (or a noise field) of the noises arriving at the target position.

In 1006, the processing device (e.g., the anti-noise determination module 806 of the processing device 140 or the ANC circuit 524) may determine anti-noise signals based on the predicted noise signals. In some embodiments, the processing device may obtain acoustic properties of the predicted noise signals, such as an energy, an amplitude, a phase, a frequency, etc. The processing device may determine the anti-noise signals based on the obtained acoustic properties. The determined anti-noise signals may have an opposite phase to the phase of the predicted noise signals, while have the same amplitude and/or the same frequency relative to the predicted noise signals. In some embodiments, a plurality of denoising parameters corresponding to the anti-noise signals may be determined. The plurality of denoising parameters may be used to direct one or more denoising units (e.g., the one or more denoising units 514 or 660) to generate sounds for cancelling the noises arriving at the target position. In some embodiments, the plurality of denoising parameters may include electrical properties (e.g., a current, a voltage, a frequency, etc.) of a current input into each of the one or more denoising units.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 1002 and 1004 may be integrated into a single operation.

Figure 11A:
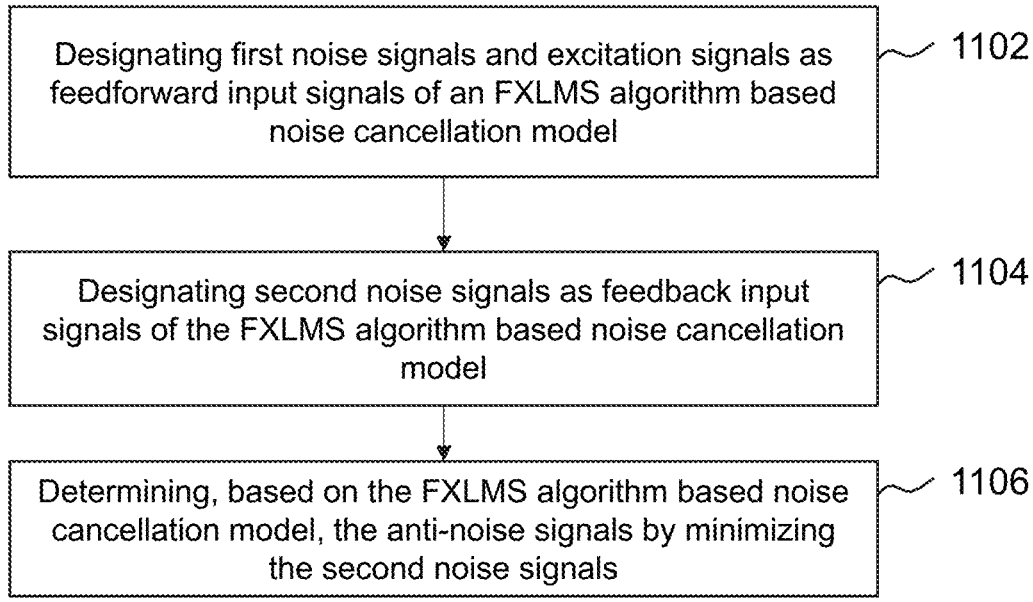
FIG. 11A is a flowchart illustrating an exemplary process for determining anti-noise signals according to some embodiments of the present disclosure.

FIG. 11A is a flowchart illustrating an exemplary process for determining anti-noise signals according to some embodiments of the present disclosure. In some embodiments, process 1100 may be implemented in the imaging system 100 illustrated in FIG. 1. For example, the process 1100 may be stored in a storage device (e.g., the storage device 150, or the storage 320 of the processing device 140) as a form of instructions, and can be invoked and/or executed by the processing device 140 (e.g., the processor 310 of the processing device 140, one or more processing circuits illustrated in FIG. 5, or one or more modules in the processing device 140 illustrated in FIG. 8). The operations of the illustrated process 1100 presented below are intended to be illustrative. In some embodiments, the process 1100 may be accomplished with one or more additional operations not described, and/or without one or more of the operations discussed. Additionally, the order in which the operations of the process 1100 as illustrated in FIG. 11A and described below is not intended to be limiting.

In 1102, the processing device (e.g., the anti-noise determination module 806 of the processing device 140 or the ANC circuit 524) may designate first noise signals and excitation signals as feedforward input signals of an FXLMS algorithm based noise cancellation model. The FXLMS algorithm based noise cancellation model may be described in connection with FIG. 11B.

In some embodiments, the first noise signals may be detected by a first array of noise detection units disposed inside a scanning bore of a medical imaging apparatus (e.g., an MRI apparatus). In some embodiments, the first noise signals may be acoustic noises caused by the vibration of gradient coils during the MRI scanning. In some embodiments, the first noise signals may be designated as source noises inside the scanning bore. In some embodiments, the excitation signals used for the operation of the gradient coils may be obtained from an excitation circuit (e.g., the excitation circuit 522). The excitation signals may include electrical signals associated with a pulse sequence, a section thickness, a field of view (FOV), repetition time (TR), echo time (TE), or the like, or any combination thereof. Compared with traditional FXLMS algorithm for active noises control, as used herein, the detected first noise signals and the excitation signals may be taken as the joint feedforward inputs of the FXLMS algorithm.

In 1104, the processing device (e.g., the anti-noise determination module 806 of the processing device 140 or the ANC circuit 524) may designate second noise signals as feedback input signals of the FXLMS algorithm based noise cancellation model.

In some embodiments, the second noise signals may be detected by a second array of noise detection units near (or around) the target position. In some embodiments, the second noise signals may include error noise signals, which is the net response of the original acoustic noises (e.g., the first noise signals) and sounds produced by one or more denoising units. For example, the error noise signals can be the sum of the sounds and the first noise signals arriving at the target position. In some embodiments, the second noise signals may include a portion of the first noise signals which cannot be eliminated by the one or more denoising units.

In 1106, the processing device (e.g., the anti-noise determination module 806 of the processing device 140 or the ANC circuit 524) may determine, based on the FXLMS algorithm based noise cancellation model, the anti-noise signals by minimizing the second noise signals.

Figure 11B:
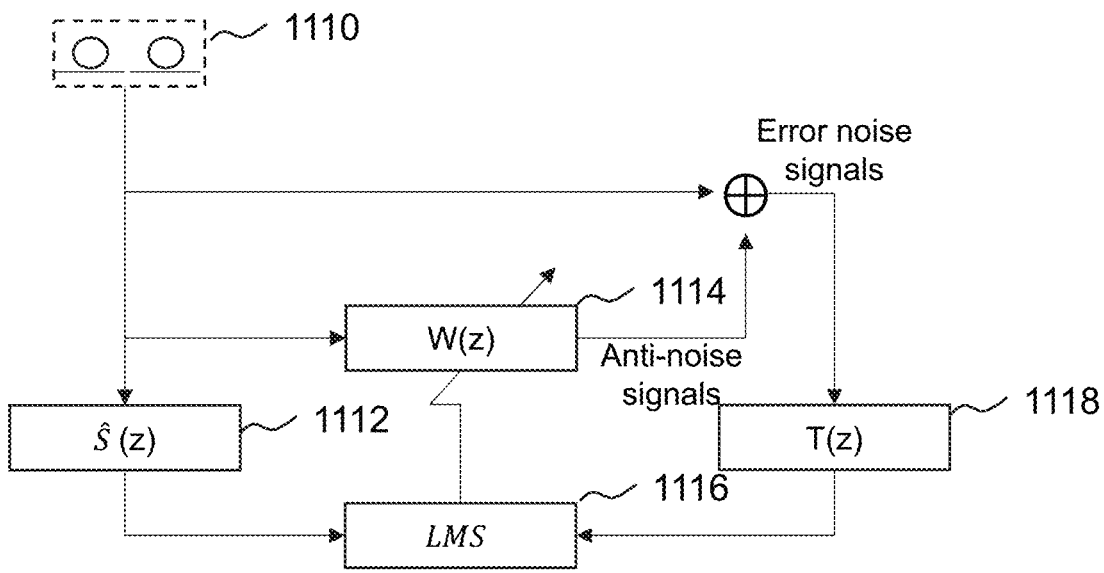
FIG. 11B is a block diagram illustrating a filtered-x least mean squares (FXLMS) algorithm based noise cancellation model according to some embodiments of the present disclosure.

Referring to FIG. 11B, which illustrates the FXLMS algorithm based noise cancellation model according to some embodiments of the present disclosure. Reference signals 1110 may include the first noise signals detected by the first array of noise detection units and excitation signals used for the operation of the gradient coils. The error noise signals (i.e., the detected second noise signals) may be detected by the second array of noise detection units. For the FXLMS algorithm, the reference signals 1110 may be used as the feedforward inputs and the error noise signals may be used as the feedback inputs. A transfer function $\hat{S}(z)$ 1112 may indicate noise transfer characteristics of a first transmitting path. The first transmitting path may refer to a process in which the anti-noise signals (or the sounds) output from the one or more denoising units reaches the second array of noise detection units. A transfer function $T(z)$ 1118 may indicate noise transfer characteristics of a second transmitting path. The second transmitting path may refer to a process in which the anti-noise signals (or the sounds) output from the one or more denoising units reaches the target position (e.g., a position of the ears). In some embodiments, the transfer functions $\hat{S}(z)$ and $T(z)$ may be measured in advance. The least mean square (LMS) module 1116 may apply the transfer functions $\hat{S}(z)$ and $T(z)$, and determine a filtering parameter to set output anti-noise signals of the one or more denoising units. A filter function $W(z)$ may generate the anti-noise signals by using the reference signals 1110 and the output value (e.g., the filtering parameter) of the LMS 1116. In response to the anti-noise signals, the one or more denoising units may generate corresponding sounds for cancelling the noises arriving at the target position. In some embodiments, the filter function $W(z)$ may coverage by minimizing the error noise signals until the error noise signals are equal to or less than a threshold. When the filter function converges, optimal anti-noise signals can be generated. In some embodiments, the filter function $W(z)$ may include an adaptive filter related filtering function.

Figure 12:
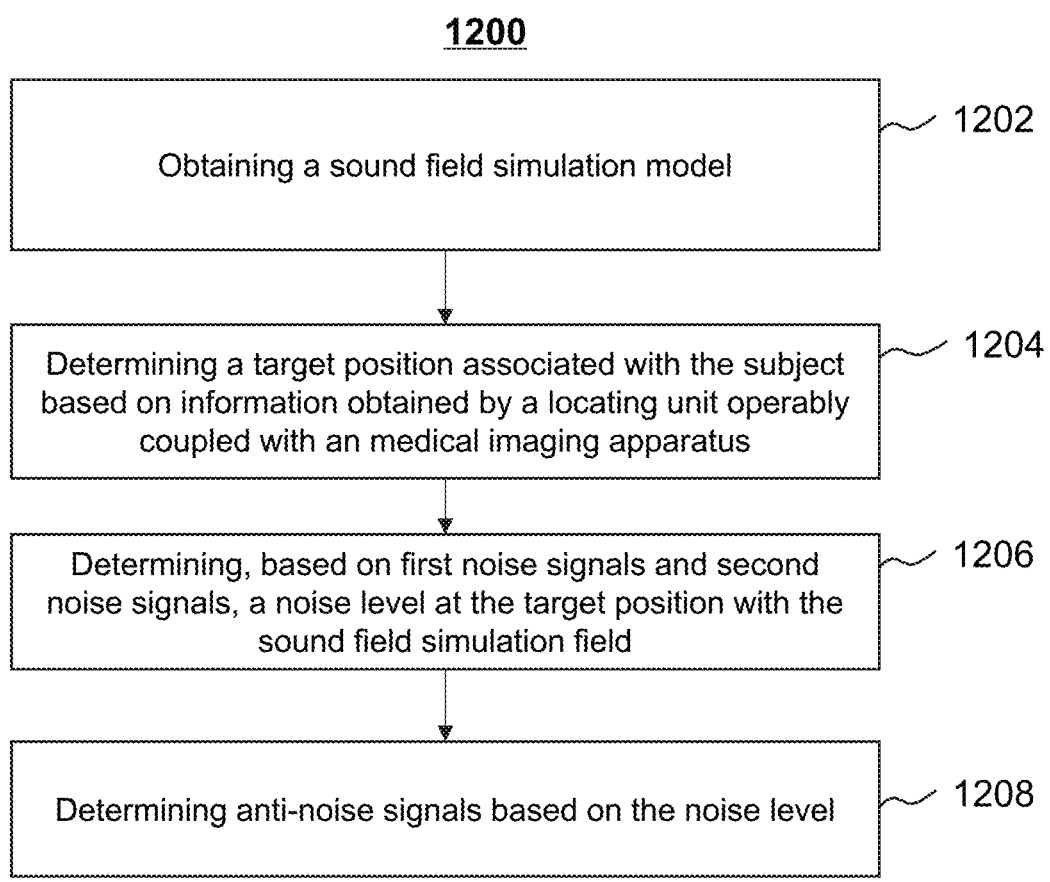
FIG. 12 is a flowchart illustrating an exemplary process for determining anti-noise signals according to some embodiments of the present disclosure.

FIG. 12 is a flowchart illustrating an exemplary process for determining anti-noise signals according to some embodiments of the present disclosure. In some embodiments, process 1200 may be implemented in the imaging system 100 illustrated in FIG. 1. For example, the process 1200 may be stored in a storage device (e.g., the storage device 150, or the storage 320 of the processing device 140) as a form of instructions, and can be invoked and/or executed by the processing device 140 (e.g., the processor 310 of the processing device 140, one or more processing circuits illustrated in FIG. 5, or one or more modules in the processing device 140 illustrated in FIG. 8). The operations of the illustrated process 1200 presented below are intended to be illustrative. In some embodiments, the process 1200 may be accomplished with one or more additional operations not described, and/or without one or more of the operations discussed. Additionally, the order in which the operations of the process 1200 as illustrated in FIG. 12 and described below is not intended to be limiting.

In 1202, the processing device (e.g., the acquisition module 802 of the processing device 140 or the ANC circuit 524) may obtain a sound field simulation model. In some embodiments, the sound field simulation model may be configured to model a noise field (or a sound field) inside a scanning bore of a medical imaging apparatus (e.g., the MRI apparatus 110). In some embodiments, the sound field simulation model may be constructed based on a geometric model of the MRI apparatus including the noise cancellation system. In the sound field simulation model, the components (e.g., the scanning bore, the RF coil, the target position associated with the subject, the first array of noise detection units, the second array of noise detection units, the one or more denoising units, etc.) may be modelled. In some embodiments, the sound field simulation model may include a finite element simulation of the sound field distribution among the components of the MRI apparatus including the noise cancellation system. In some embodiments, the sound field simulation model can be constructed by one or more commercial simulation tools (e.g., MATLAB, COMSOL Monte-Carlo simulation, etc.). In some embodiments, the sound field simulation model can be embodied in a digital signal processor (DSP), such as the ANC circuit 524.

In 1204, the processing device (e.g., the acquisition module 802 of the processing device 140) may determine a target position associated with the subject based on information obtained by a locating unit (e.g., the locating unit 680) operably coupled with the medical imaging apparatus. In some embodiments, the target position associated with the subject can refer to a position of a target portion of the subject. The target portion of the subject may include a specific portion of a body of the subject, such as the head, the thorax, the upper body, or the like, or a combination thereof. In some embodiments, the target portion of the subject may include a specific organ, such as ears, eyes, the heart, etc. In some embodiments, the at least one target portion may be a position of the ears of the subject. In some embodiments, the target position may be positioned by the location unit. As described in connection with FIG. 6, the locating unit 680 may be equipped with the MRI apparatus. For example, the location unit 680 may include a tracking sensor (e.g., an optical sensor). The locating unit 680 may be compatible with the MRI apparatus. The locating unit 680 may be positioned in the scanning bore of the MRI apparatus. For example, the locating unit 680 may be set on an inner surface of the scanning bore. The locating unit 680 may identify the ears of the subject, and determine the position (e.g., in the form of coordinates) of each ear. In some embodiments, the locating unit 680 may track the ears of the patient in real time, and generate real-time coordinates of each ear.

In 1206, the processing device (e.g., the noise determination module 804 of the processing device 140) may determine, based on first noise signals and second noise signals, a noise level at the target position with the sound field simulation model. The noise level can be indicated by acoustic properties of noises arriving at the target position, such as an energy of noise, an amplitude of noise, a phase of noise, a frequency of noise, etc. The noise level of the noises arriving at the target position may be determined according to the simulation of noise distribution output by the sound field simulation model. In some embodiments, the first noise signals may be detected by a first array of noise detection units disposed in the scanning bore. The second noise signals may be detected by a second array of noise detection units near the target position associated with the subject. The first noise signals and the second noise signals can be described as the operations 902 and 904 illustrated in FIG. 9, and not be repeated here.

In 1208, the processing device (e.g., the anti-noise determination module 806 of the processing device 140 or the ANC circuit 524) may determine anti-noise signals based on the noise level. In some embodiments, the processing device may analyze the acoustic properties indicative of the noise level, and determine the anti-noise signals based on the acoustic properties. The determined anti-noise signals may have an opposite phase to the phase of the noises arriving at the target position, while have the same amplitude and/or the same frequency relative to the noises arriving at the target position.

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, operations 1206 and 1208 may be integrated into a single operation.

Figure 13:
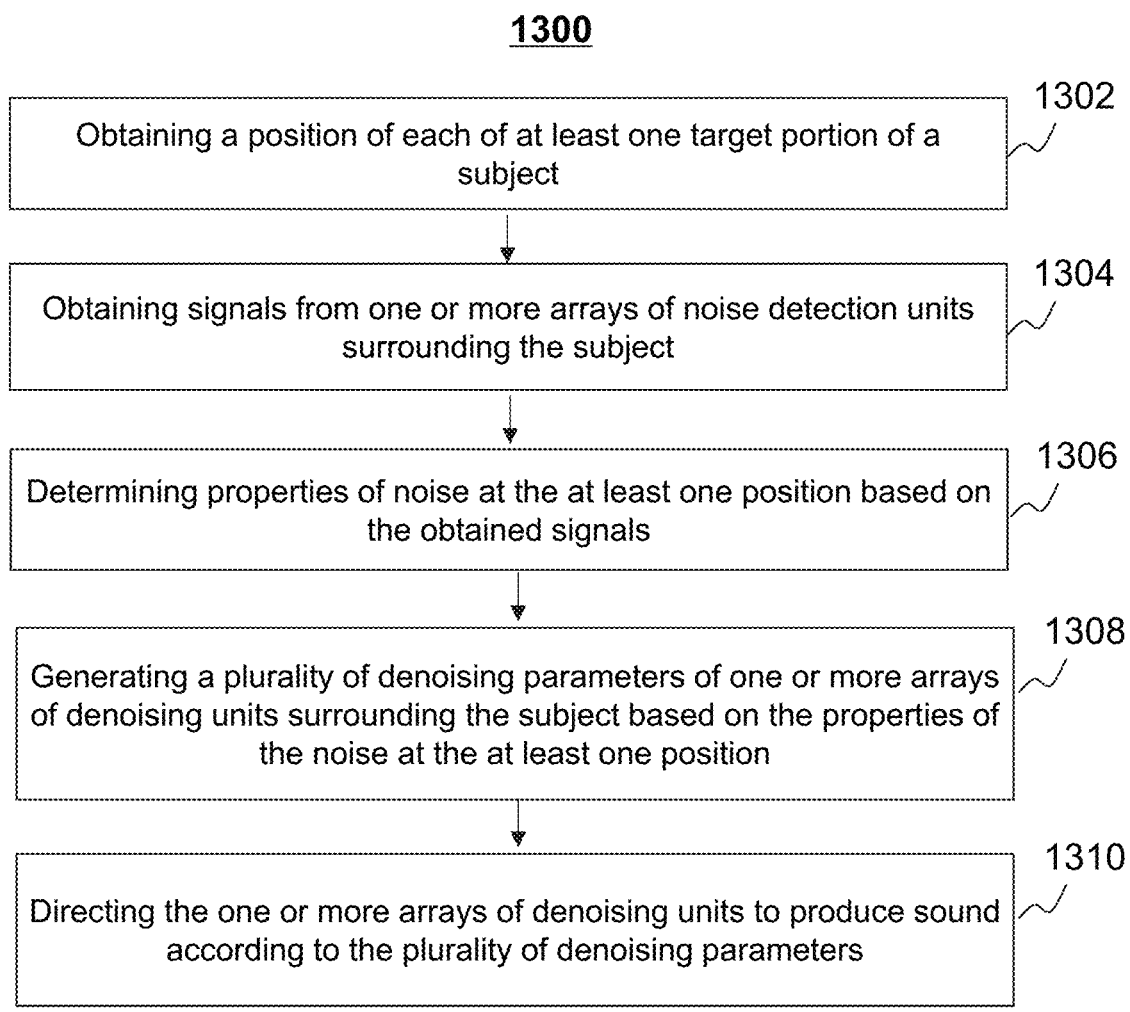
FIG. 13 is a flowchart illustrating an exemplary process for noise cancellation in an MRI system according to some embodiments of the present disclosure.

FIG. 13 is a flowchart illustrating an exemplary process for noise cancellation in the MRI system according to some embodiments of the present disclosure. In some embodiments, process 1300 may be implemented in the imaging system 100 illustrated in FIG. 1. For example, the process 1300 may be stored in a storage device (e.g., the storage device 150, or the storage 320 of the processing device 140) as a form of instructions, and can be invoked and/or executed by the processing device 140 (e.g., the processor 310 of the processing device 140, or one or more processing circuits illustrated in FIG. 5, or one or more modules in the processing device 140 illustrated in FIG. 8). The operations of the illustrated process 1300 presented below are intended to be illustrative. In some embodiments, the process 1300 may be accomplished with one or more additional operations not described, and/or without one or more of the operations discussed. Additionally, the order in which the operations of the process 1300 as illustrated in FIG. 13 and described below is not intended to be limiting.

In 1302, a position of each of at least one target portion of a subject may be obtained. Operation 1302 may be performed by the acquisition module 802.

The target portion of the subject may include a specific portion of a body of the subject, such as the head, the thorax, the upper body, or the like, or a combination thereof. In some embodiments, the target portion of the subject may include a specific organ, such as ears, eyes, the heart, etc. In some embodiments, the at least one target portion may be ears of the subject. The position of each of the at least one target portion may be obtained by a locating unit. The locating unit may identify the at least one target portion of the subject, and determine the position of each of the at least one target portion. In some embodiments, the locating unit may be a sensor (e.g., an optical sensor, such as an optical camera) capable of identifying the at least one target portion in a three-dimensional (3D) space. The locating unit may employ one or more identification algorithms (e.g., a neural network, a scale-invariant feature transform (SIFT), etc.) to identify the at least one target portion.

After the locating unit identifies the at least one target portion, a position of each of the at least one target portion may be determined. The at least one position may be determined by calculating coordinates of the at least one position relative to a 3D coordinate system (e.g., the coordinate system illustrated in FIG. 1). In some embodiments, the locating unit may focus on the at least one target portion of the subject in real time, and generate real-time coordinates of each of the at least one target portion of the subject.

In 1304, signals from one or more arrays of noise detection units surrounding the subject may be obtained. Operation 1304 may be performed by the acquisition module 802.

The noise detection units may detect sounds including acoustic noises from the environment including the position of the at least one target portion of the subject. In some embodiments, each noise detection unit may be an audio monitoring device, such as a microphone. In some embodiments, each noise detection unit may be a specialized microphone being in compatible with the MR system. For example, piezoelectric ceramics may be used in the specialized microphone such that the specialized microphone has a high fidelity. The one or more arrays of noise detection units may be positioned in the scanning region (e.g., a scanning bore 504) in a particular manner. For example, an array of noise detection units may be set on an inner surface of the scanning region as a circle surrounding the head of the subject. An example regarding the configuration of the one or more arrays of noise detection units may be provided in FIG. 6 and the descriptions thereof.

In 1306, properties of the noise at the at least one position may be determined based on the obtained signals. Operation 1306 may be performed by the noise determination module 804.

As used herein, the properties of the noise at a position refer to acoustic properties of the noise at the position, such as an energy, an amplitude, a phase, a frequency, etc. In some embodiments, the properties of the noise at the at least one position may be determined by inputting the signals of the one or more arrays of noise detection units into a sound field simulation model. In some embodiments, the sound field simulation model may be constructed by MATLAB. In some embodiments, the sound field simulation model may be embodied in a digital signal processor (DSP), etc. The sound field simulation model can be described in connection with operation 1202 and not be repeated herein.

In 1308, a plurality of denoising parameters of one or more arrays of denoising units surrounding the subject may be generated based on the properties of the noise at the at least one position. Operation 1308 may be performed by the anti-noise determination module 806. The one or more arrays of denoising units may produce sounds having particular acoustic properties at the at least one position. For example, the sounds produced by the one or more arrays of denoising units at each of the at least one position may have the same amplitude as the amplitude of the noise at each corresponding position, the same frequency as the frequency of the noise at each corresponding position, and an opposite phase (i.e., having a difference of $\pi$) relative to the phase of the noise at each corresponding position. Since the phase of the sounds produced by the one or more arrays of denoising units at each of the at least one position is opposite to the phase of the noise at each corresponding position, the noise at the at least one position may be counteracted by the sound produced by the one or more arrays of denoising units, thus reducing or eliminating the noise at the position of each of the at least one portion of the subject.

In some embodiments, each denoising unit may be a speaker, such as a non-magnet speaker. In some embodiments, each denoising unit may be a specialized speaker being in compatible with the MR system. For example, piezoelectric ceramics may be used in the specialized speaker such that the specialized speaker has a high fidelity. The one or more arrays of denoising units may be positioned set in the scanning region in a particular manner. For example, an array of noise detection units may be evenly set on a holder properly connected to a quadrature coil surrounding the head of the subject. An example regarding the configuration of the one or more arrays of noise detection units may be provided in FIG. 6 and the descriptions thereof.

In some embodiments, the plurality of denoising parameters of the one or more arrays of denoising units may include electrical properties (e.g., a current, a voltage, a frequency, etc.) of a current input into each of the one or more arrays of denoising units. In some embodiments, the sound field produced by the one or more arrays of denoising units with various denoising parameters may be simulated by the sound field simulation model. Denoising parameters under which the sound field produced by the one or more arrays of denoising units has desired acoustic properties at each of the at least one position may be determined by the sound field simulation model. For example, the denoising parameters of the one or more arrays of denoising units may be determined by inputting the configuration of the one or more arrays of denoising units and the properties of the noise at the at least one position into the sound field simulation model. In some embodiments, the denoising parameters may be determined in accordance with the FXLMS algorithm based noise cancellation model.

In 1310, the one or more arrays of denoising units may be directed to produce sound according to the plurality of denoising parameters. Operation 1310 may be performed by the sound generation module 808.

Currents of desired electrical properties may be delivered to the one or more denoising units according to the plurality of denoising parameters. The one or more arrays of denoising units may produce sound for counteracting the noise at the position of each of the at least one target portion of the subject. Specifically, the at least one target portion of the subject may be an ear or all the ears of a patient.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer-readable media having computer readable program code embodied thereon.

A computer readable signal medium may include a propagated data signal with computer readable program code embodied therein, for example, in baseband or as part of a carrier wave. Such a propagated signal may take any of a variety of forms, including electromagnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object-oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby, and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software-only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A system for active noise cancellation for a subject placed in a scanning bore of a medical imaging apparatus, comprising:
at least one storage device including a set of instructions; and
at least one processor configured to communicate with the at least one storage device, wherein when executing the set of instructions, the at least one processor is configured to direct the system to perform operations including:
obtaining a real-time position of each of at least one target portion of a subject;
obtaining signals from one or more arrays of noise detection units surrounding the subject; and
directing, based on the signals obtained from the one or more arrays of noise detection units, one or more arrays of denoising units to produce a sound to counteract noise at the real-time position of each of the at least one target portion of the subject.

2. The system of claim 1, wherein directing, based on the signals obtained from the one or more arrays of noise detection units, the one or more arrays of denoising units to produce the sound includes:
determining properties of the noise at the at least one real-time position based on the obtained signals from the one or more arrays of noise detection units;
generating a plurality of denoising parameters of the one or more arrays of denoising units surrounding the subject based on the properties of the noise at the at least one real-time position; and
directing the one or more arrays of denoising units to produce the sound according to the plurality of denoising parameters.

3. The system of claim 1, wherein the one or more arrays of denoising units include one or more piezoelectric ceramic vibration components for producing the sound.

4. The system of claim 1, wherein
the signals obtained from the one or more arrays of noise detection units includes
first noise signals detected by a first array of noise detection units disposed in the scanning bore, at least part of the first noise signals resulting from an operation of gradient coils of the medical imaging apparatus; and
second noise signals near the real-time position of each of the at least one target portion, the second noise signals being detected by a second array of noise detection units; and
directing, based on the signals obtained from the one or more arrays of noise detection units, the one or more arrays of denoising units to produce the sound includes:
determining anti-noise signals based on the first noise signals and the second noise signals; and
directing the one or more arrays of denoising units to produce the sound in accordance with the anti-noise signals.

5. The system of claim 4, wherein the anti-noise signals are determined based further on excitation signals used for the operation of the medical imaging apparatus.

6. The system of claim 5, wherein determining the anti-noise signals based on the first noise signals, the second noise signals and the excitation signals includes:
determining predicted noise signals near the at least one target portion by feeding the first noise signals, the second noise signals and the excitation signals to a target noise prediction model; and
determining the anti-noise signals based on the predicted noise signals, wherein the anti-noise signals have an opposite phase to the predicted noise signals.

7. The system of claim 5, wherein determining the anti-noise signals based on the first noise signals, the second noise signals and the excitation signals includes:

designating the first noise signals and the excitation signals as feedforward input signals of an FXLMS algorithm based noise cancellation model;

designating the second noise signals as feedback input signals of the FXLMS algorithm based noise cancellation model; and determining, based on the FXLMS algorithm based noise cancellation model, the anti-noise signals by minimizing the second noise signals.

8. The system of claim 4, wherein determining the anti-noise signals based on the first noise signals and the second noise signals includes:

determining, based on the first noise signals and the second noise signals, a noise level at the at least one target portion with a sound field simulation model; and determining the anti-noise signals based on the noise level.

9. The system of claim 1, wherein at least one of the one or more arrays of noise detection units are fitted to a support platform for supporting the subject and near the at least one target portion.

10. The system of claim 1, wherein at least one of the one or more arrays of noise detection units are fitted on a local coil associated with the at least one target portion.

11. A medical imaging apparatus comprising:

a scanning bore configured to accommodate a subject to be imaged and a support platform for supporting the subject;

a locating unit configured to focus on at least one target portion of the subject in real time to generate a real-time position of each of the at least one target portion;

one or more arrays of noise detection units configured to detect signals surrounding the subject;

one or more arrays of denoising units configured to produce a sound to counteract noise at the real-time position of each of the at least one target portion of the subject; and a processing circuit configured to direct, based on the signals detected by the one or more arrays of noise detection units, the one or more arrays of denoising units to produce the sound.

12. The medical imaging apparatus of claim 11, wherein to direct the one or more arrays of denoising units to produce, based on the signals obtained from the one or more arrays of noise detection units, the sound, the processing circuit is configured to:

determine properties of the noise at the at least one real-time position based on the obtained signals from the one or more arrays of noise detection units;

generate a plurality of denoising parameters of the one or more arrays of denoising units surrounding the subject based on the properties of the noise at the at least one real-time position; and direct the one or more arrays of denoising units to produce the sound according to the plurality of denoising parameters.

13. The medical imaging apparatus of claim 11, wherein the one or more arrays of denoising units include one or more piezoelectric ceramic vibration components for producing the sound.

14. The medical imaging apparatus of claim 11, further comprising gradient coils configured to generate gradient magnetic fields;

wherein the one or more arrays of noise detection units include a first array of noise detection units disposed in the scanning bore and configured to detect first noise signals, at least part of the first noise signals resulting from an operation of the gradient coils;

a second array of noise detection units disposed near the at least one target portion and configured to detect second noise signals; and to direct the one or more arrays of denoising units to produce, based on the signals obtained from the one or more arrays of noise detection units, the sound, the processing circuit is configured to:

determine anti-noise signals based on the first noise signals and the second noise signals; and direct the one or more arrays of denoising units to produce the sound in accordance with the anti-noise signals.

15. The medical imaging apparatus of claim 14, wherein the anti-noise signals are determined based further on excitation signals used for the operation of the medical imaging apparatus.

16. The medical imaging apparatus of claim 15, wherein to determine the anti-noise signals based on the first noise signals, the second noise signals and the excitation signals, the processing circuit is configured to:

determine predicted noise signals near the at least one target portion by feeding the first noise signals, the second noise signals and the excitation signals to a target noise prediction model; and determine the anti-noise signals based on the predicted noise signals, wherein the anti-noise signals have an opposite phase to the predicted noise signals.

17. The medical imaging apparatus of claim 15, wherein to determine the anti-noise signals based on the first noise signals, the second noise signals and the excitation signals, the processing circuit is configured to:

designate the first noise signals and the excitation signals as feedforward input signals of an FXLMS algorithm based noise cancellation model;

designate the second noise signals as feedback input signals of the FXLMS algorithm based noise cancellation model; and determine, based on the FXLMS algorithm based noise cancellation model, the anti-noise signals by minimizing the second noise signals.

18. The medical imaging apparatus of claim 14, wherein to determine the anti-noise signals based on the first noise signals, the second noise signals and the excitation signals, the processing circuit is configured to:

determine, based on the first noise signals and the second noise signals, a noise level at the at least one target portion with a sound field simulation model; and determine the anti-noise signals based on the noise level.

19. The medical imaging apparatus of claim 11, wherein at least one of the one or more arrays of noise detection units are fitted on a local coil associated with the at least one target portion.

20. A method for active noise cancellation for a subject placed in a scanning bore of a medical imaging apparatus, implemented on a machine including one or more processors and one or more storage devices, the method comprising:

obtaining a real-time position of each of at least one target portion of a subject;

obtaining signals from one or more arrays of noise detection units surrounding the subject; and directing, based on the signals obtained from the one or more arrays of noise detection units, one or more arrays of denoising units to produce a sound to counteract noise at the real-time position of each of the at least one target portion of the subject.

\* \* \* \* \*